United States Patent [19]

Okabayashi et al.

[11] Patent Number: 5,468,738

[45] Date of Patent: Nov. 21, 1995

[54] FUNGICIDE AND ITS USE

[75] Inventors: Minahiro Okabayashi; Zhi-ping Bai, both of Tsukuba, Japan

[73] Assignee: Tokuyama Corporation, Yamaguchi, Japan

[21] Appl. No.: 121,319

[22] Filed: Sep. 15, 1993

[30] Foreign Application Priority Data

Sep. 16, 1992 [JP] Japan .................................. 4-246814
Sep. 16, 1992 [JP] Japan .................................. 4-246815
Mar. 30, 1993 [JP] Japan .................................. 5-071889

[51] Int. Cl.$^6$ .................... A01N 55/10; A01N 25/08; C09D 5/14

[52] U.S. Cl. .................... 514/63; 424/405; 424/409; 424/417; 424/419; 424/421; 424/484; 424/485; 424/489; 424/490; 424/496; 424/500; 424/501; 523/122; 106/16; 106/18.32; 514/495

[58] Field of Search .................... 514/63, 495; 556/9; 424/405, 409, 417, 419, 421, 484, 485, 489, 490, 496, 500, 501; 523/122; 106/16, 18.32

[56] References Cited

U.S. PATENT DOCUMENTS

| | | | |
|---|---|---|---|
| 4,400,326 | 8/1983 | Daudt et al. | .......................... 260/429 |
| 4,448,694 | 5/1984 | Plueddemann | .......................... 210/682 |
| 5,413,789 | 5/1995 | Hagiwara et al. | .......................... 424/409 |

FOREIGN PATENT DOCUMENTS

| | | |
|---|---|---|
| 3828755 | 3/1990 | Germany . |
| 3193707 | 8/1991 | Japan . |
| 4178433 | 6/1992 | Japan . |

OTHER PUBLICATIONS

Klonkowski, A. et al., "Cu (II) Complexes in organically modified silicate gels," Journal of Non–Crystalling Solids, vol. 129, 1991, pp. 101–108.

Primary Examiner—Allen J. Robinson
Assistant Examiner—John D. Pak
Attorney, Agent, or Firm—Wenderoth, Lind & Ponack

[57] ABSTRACT

A fungicide containing, as an active ingredient, a metal complex of the formula (I), $$[M\{W-Si(OA^1)_k A^2_{3-k}\}_g]Z_f \qquad (I)$$

wherein $M$, $W$, $A^1$, $A^2$, $k$, $f$, $g$ and $Z$ are as defined in the bore formula (I) of claim 1; and use thereof for various fungicidal substances.

23 Claims, 7 Drawing Sheets

FUNGICIDE AND ITS USE

FIELD OF THE INVENTION

The present invention relates to a novel metal complex, an antibacterial and antifungal agent (to be generically referred to as "a fungicide" hereinafter) formed thereof and use of the fungicide. More specifically, it relates to a novel metal complex which is excellent in heat resistance, durability and practical use and has fungicidal activity, a novel fungicide and use thereof. In this specification, the term "fungicidal" denotes both of "antibacterial" and "antifungal".

PRIOR ART

In recent years, fungicides which can be immobilized on the surfaces of various substances (to be referred to as "immobilized fungicide" hereinafter) and fungicidal inorganic particles prepared by immobilizing ions of metal such as silver or copper on zeolite or soluble glass are increasingly used as low-toxicity fungicides in many fields.

As the immobilized fungicides, there are known silicon type immobilized fungicides such as 3-(trimethoxysilyl)propyldimethyl-octadecylammonium chloride and polymer immobilized fungicides obtained by introducing quaternary ammonium salt, alkylpyridinium salt or biguanides into polymer chains.

The silicon type immobilized fungicide has characteristic features in that it can be immobilized on surfaces of various substances, and that it shows low toxicity after immobilized since it contains no soluble components. Since, however, no soluble components are contained, the fungicidal activity is exhibited in a limited site where the fungicide is immobilized. Further, there is a report that the fungicide which has formed a condensate by hydrolysis does not exhibit fungicidal activity. Therefore, the use thereof is limited in some applications. The polymer immobilized fungicide is suitable for imparting a polymer with fungicidal activity. However, its use is limited to polymers, and further, the defect with it is that a fungicidally active group is required to be introduced into a polymer chain in synthesizing a polymer.

On the other hand, the fungicidal inorganic particles obtained by immobilizing fungicidal metal ions of silver or copper on zeolite or soluble glass exhibit fungicidal activity when a very small amount of metal ions in the particles are dissociated. Therefore, the fungicidal activity extends around the particles, and as a result, a polymer can be imparted with fungicidal activity by mixing the fungicidal inorganic particles with the polymer. However, the fungicidal inorganic particles that are already known are poor in durability, and the material for the particles is limited to inorganic ion-exchanged materials. It is therefore difficult to control the particle form, particle diameter and particle distribution, and the fungicidal inorganic particles should be so improved in many ways.

The following publications constitute the background of the fungicidal metal complex of the present invention.
(1) Journal of Non-Crystalline Solid, 129 (1991) 101–108
The above publication describes that 3-(2-aminoethylamino)-propyltrimethoxysilane reacts with $Cu(NO_3)_2 \cdot 3H_2O$ to form a Cu complex and that a modified silicate gel containing Cu complex is formed by polymerizing the above Cu complex in tetramethoxysilane by a sol-gel method. However, the above publication does not describe anything concerning the physiological and pharmacological activities of the above Cu complex and modified silicate gel.

(2) JP-A-63-154746
The above publication discloses a fungicide film containing dispersions of zeolite allowed to contain a fungicide metal ion by ion exchange and a moisture absorbent.
(3) JP-A-3-81369
The above publication discloses a fungicide polymer composition obtained by mixing a zeolite powder whose particles support an ammine or amine complex of a fungicide metal with an organic polymer. This publication describes that the ligand which forms a complex with the above metal includes ammonia and ethylenediamine.
(4) JP-A-3-193707
The above publication discloses a fungicide silicate obtained by replacing an ion-exchangeable metal of a laminar silicate (typified by sodium montmorillonite) with a coordination compound of a metal such as silver or copper and an organic ligand. This publication describes ethylenediamine, phenanthoroline and dipyridyl as organic ligands.
(5) JP-A-4-13733
The above publication discloses an aseptic film obtained by the corona discharge treatment of the surface of a film formed of a resin containing aluminosilicate into which a fungicide metal ion has been introduced by ion-exchange. The invention of this publication seeks to realize higher fungicidal activity on the film surface by depositing a larger amount of a fungicide metal on the film surface by corona discharge treatment.
(6) JP-A-4-173244
The above publication discloses a fungicide multi-layered film whose surface layer is a film containing an inorganic fungicidal substance (e.g., ammine of silver or ethanolammine of silver).
(7) JP-A-4-178433
The above publication discloses a fungicide resin film prepared by dispersing soluble glass powder containing silver ion in a resin.
(8) J. Antibact. Antifung. Agents, Japan,
Vol. 20, No. 8, pp. 413–418 (1992)
The above publication shows the result of a comparison between the fungicidal activity of zeolite supporting 2.5 wt. % silver and the fungicidal activity of montmorillonite supporting silver ion chelated with 2,4-thiazolylbenzoimidazole (abbreviated as TBZ). In the result, the fungicidal activity of montmorillonite supporting silver chlelated with TBZ is lower than that of zeolite supporting silver. The writer of the above publication concludes that the activity of silver ion is shielded by chelating.

As shown in the above publications, most of the fungicidal inorganic particles that have been already known are obtained by immobilizing fungicidal metal ion on ion-exchangeable particles (e.g., zeolite) by ion exchange or by immobilizing fungicidal metal ion on ion-exchangeable particles by ion exchange while the metal ion has the form of an ammine complex or an amine complex. These fungicidal inorganic particles are mainly dispersed in resins before use.

Since, however, in the above known fungicidal inorganic the particles, the fungicidal metal ion is immobilized on the particle by ion exchange, the metal ion is liable to be dissociated, and it is difficult to maintain constant fungicidal activity for a long period of time. Another defect is that although the amount of metal ion immobilized by ion exchange is large, the fungicidal inorganic particles only show low fungicidal activity when actually used. Further, most of the ion-exchangeable particles (e.g., zeolite) are active, and when they are dispersed in the resins, silver oxide tends to form to cause coloring.

On the other hand, in particles on which a fungicide metal in the form of an ammine complex or an amine complex is immobilized by ion exchange, the metal ion is not so easily dissociated as the metal ion of particles on which a metal is directly immobilized by ion exchange. However, the above particles have the following problems in practical use. Some ligands of the complex decrease the fungicidal activity of the metal ion, or coloring or discoloration occurs after a long period of time.

Further, for conventional fungicidal inorganic particles, an ion exchange reaction is used as immobilization means, and the object material (particles) on which the fungicidal inorganic particles can be immobilized are limited.

SUMMARY OF THE INVENTION

It is an object of the present invention to provide a fungicide which can constantly exhibit its fungicidal activity for a long period of time.

It is a second object of the present invention to provide a fungicide which contains a relatively small amount of a fungicide metal but has high fungicidal activity.

It is a third object of the present invention to provide a fungicide which is free from coloring and discoloration caused with the passage of time.

It is further another object of the present invention to provide a fungicide which can be immobilized on surfaces of a variety of substances.

It is further another object of the present invention to provide a fungicide which can exhibit high fungicidal activity and does not affect the properties of the resin when dispersed in the resin.

It is further another object of the present invention to provide a fungicide which is free from any toxicity problem and highly safe when used in a food packaging material or applied to home use.

It is further another object of the present invention to provide a fungicide which retains its fungicidal activity and has heat resistance and dispersibility when dispersed in a resin.

According to the present invention, the above objects and advantages of the present invention are achieved by a fungicide containing, as an active ingredient, a metal complex of the formula (I), $$[M\{W-Si(OA^1)_k A_3^2{}_{-k}\}_g]Z_f \qquad (I)$$

wherein:

M is silver ion, copper ion or zinc ion, each of $A^1$ and $A^2$ is independently a lower alkyl group, f is 1 or 2, k is an integer of 1 to 3, g is an integer of 1 to 6, Z is an anion, and W is a group of the formula (a-1) or (a-2),

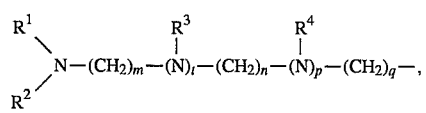

each of $R^1$, $R^2$, $R^3$ and $R^4$ is independently a hydrogen atom, a lower alkyl group or a lower aminoalkyl group, or $R^1$ and $R^2$ together may form a group of the formula

—CH$_2$CH$_2$NHCH$_2$CH$_2$—, m is 0, 2 or 3, t is 0 or 1, n is 0, 2 or 3, p is 0 or 1, q is an integer of 1 to 6, r is 0, 1 or 2, and X is a nitrogen-containing heterocyclic group, provided that when p in the formula (a-1) is 0, n is 0, that when t in the formula (a-1) is 0, m is 0, and that when r in the formula (a-2) is 0, p is 0, or metal complex immobilized particles obtained by immobilizing the above metal complex on solid particle surfaces.

In the fungicide of the present invention, both the metal complex of the above formula (I) and particles obtained by immobilizing the metal complex of the above formula (I) on solid particle surfaces similarly exhibit excellent fungicidal activity.

In particular, in the particles obtained by immobilizing the metal complex of the formula (I) on solid particle surfaces, metal complexes bond to a solid surface by a reaction of the alkoxysilyl group of the metal complex of the formula (I) and fungicidal metals strongly therefore strongly bond to, and are uniformly dispersed on, the particle surface. In the metal complex immobilized particles, therefore, the metals are dissociated to a lesser degree, and the metal complex immobilized particles exhibit high fungicidal activity even when the metal content is low. Further, the metal complex immobilized particles can exhibit fungicidal activity for a long period of time.

The fungicide of the present invention and its use will be explained more in detail hereinafter.

Metal complex

The metal complex used as an active ingredient in the fungicide of the present invention has the formula (I) above. In the formula (I), M is a fungicidal metal ion which is selected from silver ion (Ag), copper ion (Cu) and zinc ion (Zn). In the coordination of nitrogen atom in W to M, the nitrogen atom generally coordinates to M. The fungicide of the present invention is excellent in fungicidal activity when M is silver ion or copper ion, and it is the most excellent in many ways when M is silver ion.

In the formula (I), each of $A^1$ and $A^2$ is independently a lower alkyl group. The lower alkyl group properly includes an alkyl group having 1 to 5 carbon atoms, and an alkyl group having 1 or 2 carbon atoms is the most preferred. In the formula (I), k is an integer of 1 to 3, preferably 2 or 3, particularly preferably 3.

In the formula (I), Z is an anion, and Z is a counter ion to M. Z is generally derived from an anion (Z) of a compound used as a source of M and Z in the production of the metal complex of the formula (I). Specific examples of Z include halogen ions such as chloride ion, bromide ion and iodide ion, nitrate ion, perchlorate ion, sulfate ion and hydroxide ion. f represents the number of Z ion(s), and is 1 or 2. In the metal complex of the formula (I), the charge of the metal ion (M) and the sum of the charge of the counter ion(s) Z balance with each other.

In the formula (I), W is a group of the following formula (a-1) or (a-2). W is the site where the fungicidal metal M is coordinated.

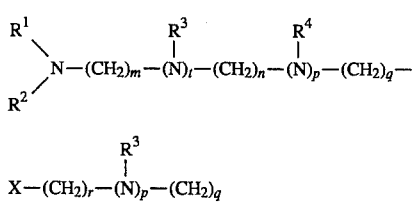

(a-1)

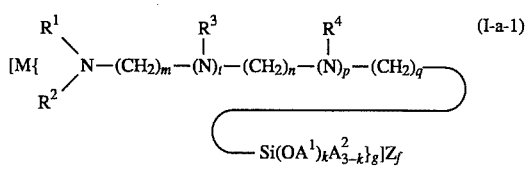

(a-2)

In the above formula (a-1), each of $R^1$, $R^2$, $R^3$ and $R^4$ is independently a hydrogen atom, a lower alkyl group or a lower aminoalkyl group, while a hydrogen atom is preferred. When each of $R^1$ to $R^4$ is a lower alkyl group or a lower aminoalkyl group, the lower alkyl group or the alkyl group moiety of the aminoalkyl group has 1 to 5 carbon atoms, preferably 1 to 2 carbon atoms. Further, $R^1$ and $R^2$ together may form a group of the formula —$CH_2CH_2NHCH_2CH_2$—. m is 2 or 3. n is 0, 2 or 3. t is 0 or 1. p is 0 or 1, preferably 0. q is an integer of 1 to 6, preferably 2 or 3. t is 0 or 1. In the group of the formula (a-1), however, n is 0 when p is 0, and m is 0 when t is 0.

When W is tile group of the formula (a-1), the metal complex of the formula (1) is specifically represented by the following formula (I-a-1).

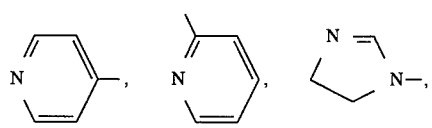

(I-a-1)

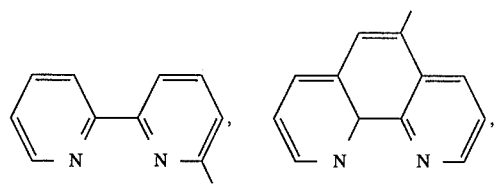

wherein M, $R^1$, $R^2$, $R^3$, $R^4$, $A^1$, $A^2$, Z, f, g, m, n, p, q, t and k are as defined in the above formula (I).

In the above formula (a-2), r is 0, 1 or 2, preferably 0. p is 0 or 1, preferably 0. q is an integer of 1 to 6, preferably 2 or 3. When r in the formula (a-2) is 0, p is 0 and M is silver ion or copper ion, preferably silver ion. $R^3$ is as defined in the above formula (a-1).

In the formula (a-2), X is a nitrogen-containing heterocyclic group, preferably 5-membered or 6-membered heterocyclic ring containing 1, 2 or 3 nitrogen atoms. The 5-membered heterocyclic group preferably includes oxazole, imidazole, dihydroimidazole, pyrazole, furazane and triazole. The 6-membered heterocyclic group preferably includes pyridine, pyrimidine, acridine, pyrazine, pyridazine, phenanthoroline, bipyridine, quinoline, purine and triazine. Specific examples of the heterocyclic group includes the following.

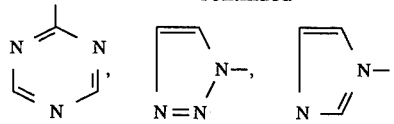

-continued

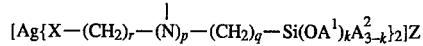

Of the above specific examples, preferred are pyridine and dihydroimidazole.

When W is the group of the formula (a-2), the metal complex of the formula (I) is specifically represented by the following formula (I-a-2).

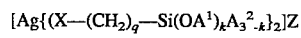

(I-a-2)

$[Ag\{X-(CH_2)_r-(N)_p-(CH_2)_q-Si(OA^1)_kA^2_{3-k}\}_2]Z$ wherein X, $R^3$, $A^1$, $A^2$, Z, r, p, q and k are as defined in the formula (I).

The metal complex of the above formula (I-a-2) is preferably represented by the following formula.

$[Ag\{(X-(CH_2)_q-Si(OA^1)_kA^2_{3-k}\}_2]Z$ wherein X, $A^1$, $A^2$, Z, q and k are as defined in the formula (I).

In the metal complex of the present invention, $\{(W-Si(OA^1)_kA^2_{3-k}\}$ is the moiety which has a group capable of coordinating to metal ion and has an alkoxysilyl group which can bond to a solid surface. In the present specification, this moiety is referred to as "ligand compound".

Specific examples of the ligand compound are preferably as follows.

| Compound No. | Chemical structure |
|---|---|
| No. 1 | —$CH_2CH_2Si(OCH_3)_3$ (abbreviated as TMSEPYD) |
| No. 2 | $N-CH_2CH_2CH_2Si(OC_2H_5)_3$ (abbreviated as TESPIMD) |
| No. 3 | $H_2N(CH_2)_3Si(OCH_3)_3$ |
| No. 4 | $H_2N(CH_2)_2NH(CH_2)_3Si(OCH_3)_3$ (abbreviated as TMSPEDA) |
| No. 5 | $H_2N(CH_2)_2NH(CH_2)_2NH(CH_2)_3Si(OCH_3)_3$ |
| No. 6 | $H_2N(CH_2)_2NH(CH_2)_2NH(CH_2)_2(CH_2)_3Si(OCH_3)_3$ |
| No. 7 | $H_2N(CH_2)_2NH(CH_2)_3Si(OCH_3)_3$ |
| No. 8 | $H_2N(CH_2)_3Si(OC_2H_5)_3$ |
| No. 9 | $H_2N(CH_2)_2NH(CH_2)_3Si(OC_2H_5)_3$ |
| No. 10 | $H_2N(CH_2)_2NH(CH_2)_2NH(CH_2)_3Si(OC_2H_5)_3$ (abbreviated as TMSPDETA) |
| No. 11 | $H_2N(CH_2)_3Si(CH_3)(OC_2H_5)_2$ |
| No. 12 | $H_2N(CH_2)_2NH(CH_2)_3Si(CH_3)(OC_2H_5)_2$ |
| No. 13 | $H_2N(CH_2)_2NH(CH_2)_2NH(CH_2)_3Si(CH_3)_2(OC_2H_5)$ |

Of the above ligand compounds, preferred are Compounds Nos. 1, 2, 4, 7 and 10.

Typical examples of the metal complex of the present invention are as follows.

$[Ag(TMSPEDA)_2]NO_3$ $[Ag(TMSPDETA)_2]NO_3$ $[Cu(TMSPEDA)_2](NO_3)_2$,

[Cu(TMSPEDA)$_2$]NO$_3$,

[Cu(TMSPDETA)$_2$](NO$_3$)$_2$,

[Cu(TMSPDETA)$_2$]NO$_3$

[Ag(TMSEPYD)$_2$]NO$_3$,

[Ag(TESPIMD)$_2$]NO$_3$

Production of metal complex

The method for the production of the metal complex of the present invention is not specially limited, while facile methods can be employed depending upon combinations of the ligand compound {W—Si(OA$^1$)$_k$A$_3{}^2{}_{-k}$} and metal compounds as sources for the fungicidal metal ion [M]. For example, the metal complex of the present invention can be produced by a method in which the ligand compound of the above formula and optionally a catalyst are added to a solution of a metal compound in a solvent.

The above metal compound which serves as a source for the fungicidal metal ion can be selected from metal compounds reactive with the ligand compound without any limitation. Specific examples of the metal compound include metal halides such as cupric chloride, cuprous chloride and zinc chloride; metal nitrates such as zinc nitrates, silver nitrates and copper nitrates; acetylacetonate metal complexes such as zinc bis(acetylacetonate); perchlorates such as silver perchlorate and zinc perchlorate; and metal alkoxide compounds such as copper diisopropoxide and zinc diethoxide.

The above catalyst can be selected from known catalysts such as acids, alkalis and charcoal.

The above solvent can be selected from known solvents which do not hydrolyze the alkoxysilyl group of the ligand compound of the formula {W—Si(OA$^1$)$_k$A$_3{}^2{}_{-k}$}. Examples of the solvent include alcohols such as methanol, ethanol and isopropanol, aromatic hydrocarbons such as benzene, toluene and xylene; halides such as dichloromethane, trichloromethane and tetrachloromethane; ethers such as diethyl ether and ethyl methyl ether; and ketones such as acetone, acetyl acetone and ethyl methyl ketone.

For the production of the metal complex, the amount ratio (molar ratio) of the above metal compound and the ligand compound is generally determined depending upon the kind of metal complexes to be produced. For example, for the production of a metal complex in which two ligand compounds coordinate to one fungicidal metal ion, the metal compound:ligand compound molar ratio is set at 1:2.

The temperature and time required for a reaction for forming the metal complex from the above metal compound and the above ligand compound are not specially limited. The reaction is generally carried out at a temperature between room temperature and 100° C. for several minutes to one week. The reaction time can be decreased by heating or by using the above catalyst.

The metal complex obtained by the above reaction between the metal compound and the ligand compound is purified optionally by means of an ion-exchange column, a molecular sieve column or cleaning after isolation.

The metal complex of the present invention is a complex in which the nitrogen of the ligand compound coordinates to the above fungicidal metal ion and has counter ion(s) for balance in charge to form a salt.

The chemical structure of the metal complex of the present invention can be generally determined by general chemical analysis means such as infrared absorption spectrum (IR spectrum), visible and ultraviolet absorption spectra, nuclear magnetic resonance spectrum (NMR spectrum), atomic absorption spectrum, inductively coupled high-frequency plasma analysis (ICP) and elemental analysis.

It can be determined by the means of NMR spectrum, elemental analysis and IR spectrum that the ligand compound is contained in the metal complex of the present invention. It can be determined by the means of IR and visible and ultraviolet absorption spectra that the ligand compound coordinates to the fungicidal metal ion. In IR spectrum, for example, when that group of the ligand compound which can coordinate to the fungicidal metal ion is an amino group and when the amino group coordinates to the fungicidal metal ion, the peak position shifts towards a high energy side. It can be therefore determined by IR spectrum that the amino group coordinates to the fungicidal metal ion. In visible spectrum, for example, when a transition metal ion such as copper ion forms a metal complex, an absorption peak based on d-d transition appears. The formation of the complex can be therefore determined by visible spectrum. Further, according to atomic absorption spectrum and ICP analysis, it can be determined that the fungicidal metal ion is contained in the metal complex of the present invention.

When the fungicidal metal ion contained in the metal complex of the present invention is a transition metal ion, the metal complex exhibits a vivid color and shows strong absorption in a visible region. When the fungicidal metal ion is not a transition metal ion, the metal complex may not show absorption in a visible region in some cases, although it shows absorption in ultraviolet and infrared region.

The metal complex of the present invention is generally soluble in a solvent. Since, however, the metal complex has an alkoxysilyl group, it easily undergoes polycondensation by heating or under the action of an acid, an alkali or water, and with an advance in the polycondensation, it gradually becomes insoluble. Further, the alkoxysilyl group of the metal complex of the present invention easily chemically bonds to surfaces of various substances such as ceramics, glass and paper. After the metal complex of the present invention bonds to the surfaces of the above substances, it shows no change in the fungicidal activity.

Metal complex immobilized particles and production thereof

The metal complex immobilized particles of the present invention refer to particles obtained by immobilizing the above metal complex on surfaces of insoluble solid particles.

The material, form and particle diameter of the insoluble solid particles on which the metal complex is to be immobilized (to be referred to as "solid particles" hereinafter) are not specially limited. The solid particles can be selected from any additives which are suitable for use and which can be used for immobilizing the metal complex of the present invention thereon. Preferred are solid particles whose surfaces have active groups (e.g., hydroxyl group, carboxyl group, alkoxy group, etc) reactive with the alkoxysilyl group.

Specific examples of the solid particles preferably include inorganic particles such as silica, titania, zirconia, alumina, zeolite, calcium silicate, apatite, glass and clay mineral particles. Of these, particularly preferred are inorganic solid particles of at least one of silica, titania, alumina and glass.

Of the above inorganic solid particles, silica or glass having OH group on the surface chemically bonds to the metal complex by a reaction between the OH group and the alkoxysilyl group of the metal complex. It is therefore assumed that the metal complex is immobilized on particle surfaces in such a state in which metal complex(s) chemically bonds to each solid particle surface. On the other hand, when solid particles having no OH group on the surface, such as charcoal or polystyrene, are used, metal complexes undergo polycondensation and are stably immobilized on the solid particle surface. Therefore, these solid particles may be also used in some cases.

The form of the solid particles includes forms of a sphere, a plate, a rod, a petal and the like. The average diameter of the solid particles can be properly determined depending upon use, such as the kind of a resin and the form of a molded article. The average diameter of the solid particles is generally 500 μm or less, preferably 0.01 to 100 μm.

The method of immobilizing the metal complex of the present invention on the solid particles is not specially limited. For example, the metal complex can be immobilized on surfaces of the solid particles by a wet method in which the solid particles are dispersed in a solution of the metal complex and then solid particles are separated and dried; by a dry method in which the solid particles are dispersed in a gas and then a solution of the metal complex is sprayed; or by a method in which the ligand compound is attached to the solid particles and then the fungicidal metal ion is allowed to act thereon. When porous particles are used as the solid particles, the porous particles are immersed in a solution of the metal complex and then dried, whereby metal complex immobilized particles are obtained.

In the above wet method, the concentration of the metal complex in the solution can be freely selected. For uniformly immobilizing the metal complex on surfaces of the solid particles, however, the concentration of the metal complex is preferably 30% by weight or less, more preferably 10% by weight or less, particularly preferably 5% by weight or less.

The solvent used for preparing the solution of the metal complex can be selected from those which do not hydrolyze the alkoxysilyl group of the metal complex and which do not break the bonding of the metal ion and the ligand compound. For example, the solvent is selected from alcohols such as methanol, ethanol, isopropanol and diethylene glycol; hydrocarbons such as butane, pentane, hexane, benzene and toluene; halogenated hydrocarbons such as dichloromethane, trichloromethane and carbon tetrachloride; ketones such as acetone, acetylacetone and ethyl methyl ketone; others such as acetonitrile, dimethylformamide, dimethylsulfoxide and diethyl ether.

The solid particles can be dispersed in a solution of the metal complex by various methods, such as a method in which a suspension of a mixture of the solid particles and the metal complex is vigorously stirred with a magnetic stirrer, a stirring blade-equipped motor or a homogenizer, or a method in which the solid particles are stirred with an ultrasonic cleaner. After the solid particles are dispersed, it is preferred to maintain the dispersed particles at a temperature between room temperature and 100° C. for several minutes to 24 hours so that the metal complex sufficiently bonds to, or reacts with, surfaces of the solid particles.

Then, the dispersed particles are separated from the above mixture by a method using a centrifugal separator, a filter or an evaporator. When an evaporator is used for the separation, the majority of the metal complex contained in the mixture is immobilized on surfaces of the solid particles. It is therefore preferred to predetermine the amount ratio of the solid particles and the metal complex.

Being freely set in such a range that the metal complex immobilized particles can be imparted with fungicidal activity, the amount of the metal complex per 100 parts by weight of the solid particles is preferably 0.01 to 10 parts by weight, more preferably 0.1 to 5 parts by weight.

Then, the separated solid particles are dried. The drying temperature is freely set at temperatures at which the immobilized metal complex is not heat-decomposed. The drying temperature is preferably room temperature to 400° C., more preferably room temperature to 250° C.

In the dry method, for example, the metal complex can be immobilized on surfaces of the solid particles by spraying the metal complex into a closed container in which the solid particles are dispersed in a gas.

The amount of the metal complex immobilized on the solid particles can be determined by a known method such as a method using a fluorescence X-ray analyzer or a method in which the immobilized metal complex is separated/dissolved by means of nitric acid and analyzed with a nuclear light absorption apparatus or a plasma induction analyzer.

Use of metal complex and metal complex immobilized particles

Both the above metal complex and metal complex immobilized particles according to the present invention have excellent fungicidal activity, and can be therefore used as various types of fungicides.

In one typical use, the metal complex or the metal complex immobilized particles are used as a fungicide liquid mixture prepared by dissolving or dispersing the metal complex or the metal complex immobilized particles in a liquid solvent. As already described, the metal complex is soluble in a variety of solvents, and a solution of the metal complex in a solvent can be used as such. The metal complex or the metal complex immobilized particles are used in the form of such an ordinary solution, while it is preferred to use the metal complex or the metal complex immobilized particles in the form of a spray solution since the area to which the solution is to be applied can be broadened. The solvent used for preparing the solution or spray solution is selected from those described regarding the preparation of the solution of the metal complex. Although not specially limited, the concentration of the metal complex in the solution is generally 0.0001 to 5% by weight, preferably 0.005 to 1% by weight.

For the use of the metal complex or the metal complex immobilized particles in the form of a spray solution, a propellant known per se can be used. The propellant includes low-boiling compounds such as propane, butane, liquid petroleum gas, trichoromonofluorobutane, and dimethyl ether.

Further, the metal complex or the metal complex immobilized particles according to the present invention can be used in the form of a coating solution. A dispersion of the metal complex immobilized particles is advantageously used as a coating solution. One typical coating solution is a composition containing the metal complex immobilized particles, a liquid medium and an organic polymer compound. This coating solution is applied to the surface of a film, a plate, a board or other article and then the liquid medium is volatilized, whereby a fungicide coating is formed. The concentration of the metal complex in the coating solution is 0.0001 to 1% by weight, preferably 0.0005 to 0.5% by weight, and the content of the metal complex immobilized particles in the coating solution is 0.01 to 60% by weight, preferably 0.1 to 50% by weight. The above liquid medium is preferably selected from those described regarding the preparation of the solution of the metal complex. The above organic polymer compound is selected from acrylic resin, polyester resin, polystyrene resin, vinyl acetate resin, polyurethane resin, vinyl chloride resin, cellulose acetate, polyvinylidene fluoride or the like.

The amount of the organic polymer compound in the coating solution is 1 to 60% by weight, preferably 5 to 50% by weight.

The metal complex immobilized particles according to the present invention can be advantageously applied to a fungicide molded article, a fungicide film, a fungicide container, or the like by using a dispersion of them in a resin. The metal complex immobilized particles according to the present invention has excellent heat resistance so that the fungicidal activity is not at all degraded when a resin containing a dispersion of the metal complex immobilized particles is molded. Therefore, the metal complex immobilized particles can be incorporated into any one of thermoplastic resins and thermosetting resins. In general, however, it is proper to use the metal complex immobilized particles in the form of a resin composition obtained by dispersing it in a thermoplastic resin. This resin composition can be molded into any form of a film, a plate, a laminated film, a molded article and a fiber.

The method of use of the metal complex immobilized particles in the form of a fungicide molded article obtained from a composition containing a thermoplastic resin and the metal complex immobilized particles will be explained hereinafter.

The above thermoplastic resin includes homopolymers and copolymers of α-olefins such as ethylene, propylene and butene, a mixture of at least two of these homopolymers and copolymers, a polyvinyl chloride-containing polymer, a polystyrene-containing polymer, a polyester-containing polymer, polycarbonate, a polyamide-containing polymer and a silicone-containing polymer.

The above thermoplastic resin and the metal complex immobilized particles can be mixed with a known mixing apparatus such as a Henschel mixer, a V-blender or a tumbler. The so-obtained fungicidal resin composition can be molded into pellets or rods with a single-screw extruder or a multi-screw extruder.

The amount of the metal complex immobilized particles in the fungicidal resin composition can be freely selected depending upon use of the fungicidal molded article. In general, the content of the metal complex immobilized particles in the fungicidal resin composition is 0.0001 to 60% by weight, preferably 0.001 to 50% by weight.

The so-obtained fungicidal resin composition can be molded into various articles such as pellets, a sheet, a film, a container and a pipe depending upon its use. Further, it may be used in the form of a coating composition to form a coating on a substrate.

Examples of the molded articles include film-like articles for packaging, sanitary purpose or agriculture such as a food packaging film, a porous film and a sheet for agriculture; daily or household articles such as tableware, a washbowl, a bucket, a food reserve container, a cutting board and a scourer; electrical products such as a telephone, a washing machine, a refrigerator, a humidifier and a dish dryer; fiber products such as a white robe, a mask, socks, a raincoat and working gloves; and construction materials such as wallpaper, a silicone rubber sealing material, a heat insulating sheet, artificial marble (composite resin) and an insect prevention netting.

The fungicidal resin composition of the present invention can be molded by known methods such as an injection molding method, an extrusion method, a blow molding method, a vacuum forming method, a slash molding method, an inflation method, a T-die method and a calendering method.

The fungicidal film of the present invention has at least one layer obtained by dispersing the metal complex immobilized particles in a thermoplastic resin. When the fungicidal film is a multi-layered film, at least one layer obtained by dispersing the metal complex immobilized particles in a thermoplastic resin is preferably located as an outermost layer.

The average particle diameter of the metal complex immobilized particles for use in the fungicidal film is preferably 0.1 to 10 μm. When particles suitable for the production of a film are already determined, metal complex immobilized particles can be prepared by immobilizing the metal complex on surfaces of the determined particles according to the above method.

The thermoplastic resin as a raw material for the fungicidal film is selected from known film-forming thermoplastic resins such as a homopolymer of an α-olefin such as ethylene, propylene or butene, a copolymer of at least two of such α-olefins, a mixture of at least two of these α-olefin homopolymers and copolymers, polyamide, polystyrene, polycarbonate and polyvinyl chloride.

In the fungicidal film, the amount of the metal complex immobilized particles based on the thermoplastic resin is generally 15% by weight or less, preferably 0.001 to 10% by weight.

The fungicidal film of the present invention characteristically has at least one resin layer (to be referred to as "fungicidal layer" hereinafter) formed of a resin composition prepared by dispersing the metal complex immobilized particles in a thermoplastic resin.

When, for example, food such as vegetable, fruit, bread or meat is packed with the fungicidal film, the fungicidal layer is preferably in contact with the contents directly or indirectly through water for the fungicidal film to exhibit fungicidal activity. The fungicidal film of the present invention is therefore preferably formed of a single fungicidal layer or a laminated film whose outermost layer is the fungicidal layer.

The fungicidal film of the present invention can be formed by a known film forming method such as a calendering method, an inflation method, a T-die method or a solution casting method. Further, the film may be an unstretched film, or there may be employed a monoaxial stretching method, a consecutively biaxial stretching method, a simultaneously biaxial stretching method and some other stretching method.

The fungicidal film of the present invention may contain inorganic particles of calcium carbonate, titania, silica or magnesium silicate for the improvement of its appearance or permeation to steam. Further, for heat sealability, it may also contain at least one polymer selected from a petroleum resin, polystyrene, polypropylene, polybutene, an ethylene-propylene copolymer, an ethylene-butene copolymer, a propylene-butene copolymer, an ethylene-propylene-butene copolymer, polyvinyl acetate and an ethylenevinyl acetate copolymer. The above inorganic particles and/or copolymer(s) are added in such an amount that a film can be formed.

Further, the fungicidal film of the present invention may also contain a variety of known additives such as a heat stabilizer, an antioxidant, a nucleating agent, an antistatic agent, a lubricant and an anti-blocking agent.

The above fungicidal film can be widely used for packaging, agriculture and sanitary purposes.

The fungicidal resin composition containing the metal complex immobilized particles of the present invention can be evaluated for its fungicidal activity by a known method such as an enumeration method of bacteria and a shake flask method as a test method for evaluation on antimicrobial and deodorant finish by Association of Sanitary Processing of Textile Products, a test method of growth inhibitory efficacy of antimicrobial and deodorant finished textile products by The Society of Antibacterial and Antifungal Agent, Japan, an agar plate method in American Association of Textile Chemists and Colorists (AATCC) Test Method (to be referred to as "halo test" hereinafter), an evaluation method for antimicrobial finish of textile and a mildew resistance test method (JIS Z 2911).

Studies of the present inventors have revealed that articles can be imparted with fungicidal activity by the following methods on the basis of the fungicidal activity and characteristic features of the metal complex of the present invention.

That is, according to the present invention, there is provided a method (method I) of imparting an article with fungicidal activity, which comprises;

(i) bringing a solution containing an alkoxysilane compound of the formula (II),

  (II)

wherein W, $A^1$, $A^2$ and k are as defined in the formula (I),
into contact with a surface of an article having an active group reactive with an alkoxysilyl group on the surface, thereby to immobilize the alkoxysilane compound on the surface of the article, and (ii) then, treating the surface of the article with a solution containing at least one metal compound selected from the group consisting of a silver compound, a copper compound and a zinc compound, to form a metal complex on the surface of the article.

Further, according to the present invention, there is provided a method (method II) of imparting an article with fungicidal activity, which comprises bringing a solution containing the metal complex of the formula (I) into contact with an article having an active group reactive with an alkoxysilyl group on the surface, thereby to immobilize the metal complex on the surface of the article.

In each of the above methods I and II, the metal complex of the formula (I) bonds to, and is immobilized on, the surface of an article owing to its alkoxysilyl group. Therefore, the article to which the fungicidal activity is to be imparted is not specially limited as long as the surface of the article has an active group reactive with an alkoxysilyl group. The material for the article includes metal, plastics, cotton, glass, paper, ceramics, wood and thermoplastic resins such as polyester. The article viewed from its form includes a film a sheet, a fiber and other molded articles.

In the above methods I and II, the solution containing an alkoxysilane compound of the formula (II) and the solution containing the metal complex of the formula (I) are used. The solvent used for preparing these solutions includes alcohols such as methanol, ethanol, isopropanol and diethylene glycol; hydrocarbons such as butane, pentane, hexane, benzene and toluene, halogenated hydrocarbons such as dichloromethane, trichloromethane and carbon tetrachloride; ketones such as acetone, acetylacetone and ethyl methyl ketone; and others such as acetonitrile, dimethylformamide, dimetylsulfoxide and diethyl ether.

The concentration of the above alkoxysilane compound or metal complex in the solution is generally 0.001 to 20% by weight, preferably 0.01 to 10% by weight.

In the above formula (I), the alkoxysilane compound of the formula (II) is immobilized on the article surface and then the surface of the article is treated with a solution containing at least one metal compound selected from the group consisting of a silver compound, a copper compound and a zinc compound. The above metal compound includes metal halides such as cupric chloride, cuprous chloride and zinc chloride; metal nitrates such as zinc nitrates, silver nitrates and copper nitrates; acetylacetonate metal complexes such as zinc bis(acetylacetonate); perchlorates such as silver perchlorate, silver perchlorate and zinc perchlorate; and metal alkoxide compounds such as copper diisopropoxide and zinc diethoxide.

The above methods I and II make it possible to impart a variety of articles with fungicidal activity. Further, the method I or II, particularly the method II, can be applied to a place where bacteria or mold is foreseen to occur, such as a wall, floor and ceiling of a kitchen, a rest room or a basement for preliminary prevention of bacteria and mold.

According to the present invention, further, there is provided a metal complex of the formula (I'),

  (I')

wherein:

M' is silver ion or zinc ion, each of $A^1$ and $A^2$ is independently a lower alkyl group, f is 1 or 2, k is an integer of 1 to 3, g is an integer of 1 to 6, Z is an anion, and W is a group of the formula (a-1) or (a-2),

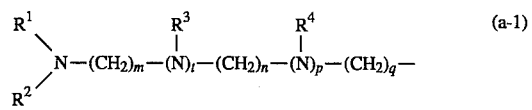  (a-1)

  (a-2)

in which:

each of $R^1$, $R^2$, $R^3$ and $R^4$ is independently a hydrogen atom, a lower alkyl group or a lower aminoalkyl group, or $R^1$ and $R^2$ together may form a group of —$CH_2CH_2NHCH_2CH_2$—, m is 0, 2 or 3, h is 0, 2 or 3, p is 0 or 1, q is an integer of 1 to 6, t is 0 or 1, r is 0, 1 or 2, and X is a nitrogen-containing heterocyclic group, provided that when p in the formula (a-1) is 0, n is 0, that when t in the formula (a-1) is 0, m is 0, and that when r in the formula (a-2) is 0, p is 0.

The metal complex of the above formula (I') is novel and can be used as an active ingredient in a fungicide. In the above formula (I'), M' is silver ion or zinc ion, and the remaining W, $A^1$, $a^2$, K and z have the same meanings as those in the formula (I).

As the metal complex of the above formula (I'), the compound of the following formula (I'-a-2) is preferred.

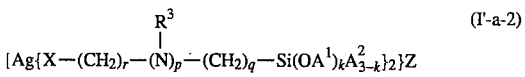  (I'-a-2)

wherein X, $R^3$, $A^1$, $A^2$, Z, r, p, q and k are as defined in the formula (I).

As the metal complex of the formula (I'-a-2), the compound of the following formula is more preferred.

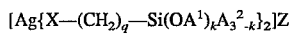

wherein X, $A^1$, $A^2$, Z, q and k are as defined in the formula (I).

As the metal complex of the above formula (I'), the compound of the following formula (I'-a-1) is also preferred.

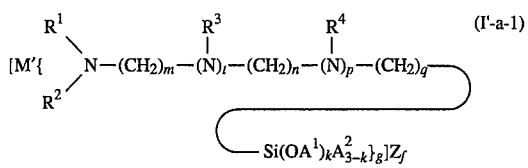

wherein M' is as defined in the formula (I') and $R^1$, $R^2$, $R^3$, $R^4$, $A^1$, $A^2$, Z, f, g, m, n, p, q, t and k are as defined in the formula (I).

In the metal complexes of the formulae (I'), (I'-a-1) and (I'-a-2), the same symbols as those in the formula (I) have the same meanings as those defined in the formula (I) except for M and M', and those defined as preferred for the symbols in the formula (I) are also preferred for the symbols in the formula (I'). Further, the method for the production of the metal complex of the formulae (I'), (I'-a-1) or (I'-a-2) is basically the same as the method for the production of the metal complex of the formula (I).

The metal complex of the present invention properly releases fungicidal metal ion and therefore exhibits fungicidal activity for a long period of time. Further, it is colorless or lightly colored. It is not optically decomposed, nor is it discolored. Its molecule contains an alkoxysilyl group, and it can be therefore chemically immobilized on surfaces of various substances. Therefore, the metal complex of the present invention can provide a fungicide excellent in both stability and durability.

The metal complex immobilized particles of the present invention exhibit excellent fungicidal activity, and differing from conventional ones, the solid particles for forming the metal complex immobilized particles are not required to have ion exchangeability and pores for supporting metal ion. Therefore, the solid particles may have any form, any composition, any particle diameter and any dispersibility. Therefore, the particles can be imparted with properties such as antiblocking properties and antistatic properties, other than fungicidal activity. For example, when a film contains metal complex immobilized particles produced by preparing spherical silica by a sol-gel method and immobilizing the metal complex of the present invention thereon, not only the metal complex exhibits fungicidal activity, but also the silica particles work as an antiblocking material.

Further, for the fungicidal resin composition of the present invention, the metal complex having metal ion as a fungicidal ingredient is used in the form in which the metal complex is immobilized on solid particles. Therefore, the metal complex can be well dispersed in the resin composition correspondingly to the dispersibility of the metal complex immobilized particles. As a result, metal ion is effectively and constantly dissociated from the fungicidal resin composition. The fungicidal effect is high and the durability is excellent even if the metal ion content is small. Further, the fungicidal resin composition of the present invention is therefore preferred in view of economic performance and environmental problems. Furthermore, for an unknown reason, the metal complex per se exhibits improved heat resistance.

Conventional organic fungicides have been poor in heat resistance, while the metal complex immobilized particles of the present invention exhibit sufficient heat resistance in a temperature range for molding thermoplastic resins. The fungicidal resin composition of the present invention, containing the fungicide having the features of both organic ones and inorganic ones, is expected to work as a novel fungicidal resin composition.

On the other hand, in view of the defect of conventional fungicidal particles, i.e., the difficulty in controlling the particle size and composition, existing particles selected as an antiblocking agent or an antistatic agent for various thermoplastic resins can be imparted with fungicidal activity by immobilizing the metal complex on such particles. It is therefore not necessary to newly determine the diameter, form and distribution of the particles for thermoplastic resins, and fungicidal resin compositions can be developed smoothly at a low cost.

The present invention will be more specifically explained with reference to Examples, although the present invention shall not be limited by the Examples.

The halo test for the evaluation of fungicides in the following Examples was carried out as follows.

Halo test

The halo test is suitable for testing the fungicidal activity of a plate, a fiber, a textile and a file such as a cloth, paper, a glass plate and ceramic. In the halo test, a test disk is attached to an flat agar medium, and an inhibition band is measured for a width after culturing. The medium was prepared as follows. A solution of 10 g of bacto-pepton and 5 g of beef extract in 1 liter of distilled water was adjusted to pH 6.8 with NaOH to obtain a culture medium. This culture medium was taken in an amount of 10 ml and placed in a test tube (12.5×17 mm) and sterilized at 120° C. at 1 arm for 20 minutes. A bacteria strain was transplanted therein and cultured at 37° C. for 24 hours to prepare a bacteria suspension. Agar in an amount of 1.5 wt. % was added to the remaining culture medium and fully dissolved. Then, the resultant solution was sterilized at 120° C. at 1 arm for 20 minutes. The solution was cooled to 45° C., and then 1 ml of the bacteria suspension was inoculated into the cooled solution to prepare a bacteria-inoculated agar culture suspension. A portion of the bacteria-inoculated agar culture suspension was placed on a plate (21×15 cm) to prepare a bacteria-inoculated agar medium. A test disk was moderately placed on the bacteria-inoculated agar medium under pressure and attached thereto. The so-obtained bacteria-inoculated agar medium with the test disk attached thereto was cultured at 37° C. for 24 hours. Then, the width of an inhibition band around the test disk was measured through the flat medium from the reverse side. The width of the inhibition band showing the fungicidal activity of the test disk was determined on the basis of the following equation. When the inhibition band is present, it shows that the test disk has fungicidal activity.

In the above test, *Staphylococcus aureus* and *Bacillus subtilis* were used. The test using yellow *Staphylococcus* is referred to as test A, and the test using *Bacillus subtilis* is referred to as test B.

$$W=(T-D)/2$$

wherein:
W=width of inhibition band (mm)
T=diameter of inhibition band including test disk (mm)
D=diameter of test disk (mm).

EXAMPLE 1

A solution of 0.34 g of anhydrous cupric chloride ($CuCl_2$) in 20 ml of ethanol and a solution of 1.33 g of trimethoxysilylpropyldiethylenetriamine in 20 ml of ethanol were mixed, and the mixture was stirred at room temperature for 1 hour. The resultant solution was filtered through a teflon filter having an opening diameter of 0.5 μm. The filtrate was subjected to a rotary evaporator to remove the solvent and obtain a blue powdery metal complex. The metal complex was identified to be [Cu(TMSPDETA)$_2$]Cl$_2$ by the absorption spectrum and IR spectrum shown in FIGS. 1 and 2.

EXAMPLE 2

A blue powdery metal complex was obtained from 2.69 g of anhydrous cupric chloride (CuCl$_2$) and 4.89 g of trimethoxysilylpropylethylenediamine in the same manner as in Example 1. The metal complex was identified to be [Cu(TMSPEDA)$_2$]Cl$_2$ by the absorption spectrum and IR spectrum shown in FIGS. 3 and 4.

EXAMPLE 3

0.50 Gram of anhydrous cuprous chloride (CuCl) was suspended in 5 ml of methanol, and 2.23 g of trimethoxysilylpropylethylenediamine was added, whereby the color of the solution gradually changed from green to blue. The reaction proceeded and CuCl was dissolved. The reaction mixture was further stirred for 30 minutes. The resultant solution was purified in the same manner as in Example 1 to give a blue powdery metal complex. This compound was identified to be [Cu(TMSPEDA)$_2$]Cl by the absorption spectrum and IR spectrum shown in FIGS. 5 and 6.

EXAMPLE 4

A solution of 2.67 g of TMSPEDA in 20 ml of methanol was added to a solution of 0.5529 g of zinc chloride (ZnCl$_2$) in 20 ml of methanol. The mixed solution was subjected to a rotary evaporator to remove the solvent and give a white powdery compound. The compound was identified to be [Zn(TMSPEDA)$_2$]Cl$_2$ by the IR spectrum shown in FIG. 7.

EXAMPLE 5

1.33 Grams of TMSPEDA was dropwise added to a solution of 0.51 g of silver nitrate (AgNo$_3$) in 30 ml of CH$_3$CN under nitrogen atmosphere. The mixture was stirred at room temperature for 4 hours, and then subjected to a rotary evaporator to remove the solvent and give a colorless liquid product. This product was identified to be [Ag(TMSPEDA)$_2$]NO$_3$ by the IR spectrum shown in FIG. 8.

EXAMPLE 6

While a dispersion of spherical silica particles (particle diameter 1.7 μm) in 50 ml of water was stirred, 0.7 g of TMSPEDA was added. The mixture was stirred for 30 minutes. Then, the mixture was filtered through a No. 5 filter paper, and then the remaining solid was washed with ethanol and dried at 110° C. for 30 minutes. The so-treated silica particles were dispersed in a 0.1N silver nitrate aqueous solution, and the dispersion was stirred for 30 minutes. Then, the silica particles were recovered by filtration, washed with ethanol and heat-treated at 110° C. for 30 minutes to give silver-immobilized silica particles (A). The silver-immobilized silica particles (A) were subjected to the halo test to show that the inhibition band had a width of 3.5 mm.

Examples 7–10

Example 6 was repeated except that the spherical silica particles were replaced with talc (supplied by Wako Purechemical Co., Ltd.), FLORITE (particle diameter 10 μm, supplied by Tokuyama Soda Kabushiki Kaisha), TOKUSIL (particle diameter 0.04 μm, supplied by Tokuyama Soda Kabushiki Kaisha) or charcoal (supplied by Wako Purechemical Co., Ltd.) to give silver-immobilized talc (2 mm), silver-immobilized FLORITE (2 mm), silver-immobilized TOKUSIL (3 mm) and silver-immobilized charcoal (2 mm). The above parenthesized figures show widths of inhibition bands by the halo test.

EXAMPLE 11

At room temperature, 100 ml of water and 1 g of TMSPEDA were placed in a 250 ml polypropylene beaker, and stirred for 15 minutes. A glass fiber paper-like filter (GA200, supplied by Toyo Roshi K.K.) was placed in the above solution, and stirred for 30 minutes. The glass fiber was dehydrated with a centrifugal dehydrator for 8 minutes, and then heat-treated at 110° C. for 30 minutes. The so-prepared glass fiber was immersed in a 0.1N silver nitrate aqueous solution for 30 minutes, dehydrated, and dried at 110° C. for 30 minutes to give a silver-immobilized glass fiber.

The above-obtained silver-immobilized glass fiber showed that the width of an inhibition band by the halo test was 1 mm.

EXAMPLES 12–13

Paper (Quantative Ashless, supplied by Toyo Roshi K.K.) and an absorbent cotton (Japanese Pharmacopoeia absorbent cotton, supplied by Pip. Fujimoto K.K.) were subjected to treatment in the same manner as in Example 6 to give a silver-immobilized paper (2 mm) and a silver-immobilized absorbent cotton (2 mm). The above parenthesized figures show widths of inhibition bands by the halo test.

EXAMPLE 14

At room temperature, 1 g of TMSPEDA was added to 100 g of water in a 250 ml polypropylene beaker, and the mixture was stirred for 15 minutes. A glass sheet (MATSUNAMI Micro Slide Glass S7214) was placed in the solution, and the solution was stirred for 30 minutes. Then, the glass sheet was washed with ethanol and dried at 110° C. for 30 minutes. The so-treated glass sheet was immersed in a 0.1N silver nitrate aqueous solution for 30 minutes, washed with ethanol and heat-treated at 110° C. for 30 minutes to give a silver-immobilized glass sheet. The silver-immobilized glass sheet showed that the width of an inhibition band by the halo test was 2 mm.

EXAMPLE 15

Antibacterial silica particles (B) were obtained in the same manner as in Example 6 except that TMSPEDA was replaced with TMSPDETA. The silver-immobilized silica particles showed that the width of an inhibition band by the halo test was 3.5 mm.

Comparative Example 1

When the same silica particles as those used in Example 6 were not subjected to any silver-immobilized treatment, they showed that the width of an inhibition band by the halo test was 0 mm.

Comparative Example 2

When the same glass fiber as that used in Example 11 was not subjected to any silver-immobilized treatment, it showed that the width of an inhibition band by the halo test was 0 mm.

EXAMPLE 16

1 Gram of [Ag(TMSPEDA)$_2$]NO$_3$ obtained in Example 5 was dissolved in a solution containing 47.5 ml of ethanol and 2.5 ml of water to prepare a fungicide (AG-1). 1 Gram of silica particles having a particle diameter of 1.7 μm were dispersed in 25 ml of the above fungicide (AG-1), and the mixture was stirred at room temperature for 20 minutes and filtered through a No. 5C filter paper. The remaining solid was washed with methanol, dried at room temperature for 24 hours and further dried at 80° C. for 1 hour to give fungicidal solid particles (P-AG-1). The fungicidal solid particles were pressed at a pressure of 200 kg with a tablet-forming machine to prepare a test disk having a diameter of 10 mm and a thickness of 1 mm. The test disk was subjected to the halo tests A and B to show that the widths of inhibition bands were both 3.5 mm.

EXAMPLE 17

2 Grams of [Cu(TMSPDETA)$_2$]Cl$_2$ obtained in Example 1 was dissolved in 98 ml of ethanol to prepare a fungicide (CU-1). 1 Gram of silica particles having a particle diameter of 2 μm were dispersed in 25 ml of the above fungicide (CU-1), and the mixture was stirred at room temperature for 20 minutes and filtered through a No. 5C filter paper. The remaining solid was dried at room temperature for 24 hours and further dried at 80° C. for 1 hour to give fungicidal solid particles (P-CU-1). The fungicidal solid particles were pressed at a pressure of 200 kg with a tablet-forming machine to prepare a test disk having a diameter of 10 mm and a thickness of 1 mm. The test disk was subjected to the halo tests A and B to show that the widths of inhibition bands were both 0.5 mm.

(AGSI-1).

10 Grams of silica particles having a particle diameter of 1.7 μm were dispersed in a mixture of 800 ml of methanol with 200 ml of 25% ammonia liquor at room temperature, and 25 ml of the fungicide (AGSI-1) was added to the above-prepared suspension with a micropump at a rate of 1 ml/minute with stirring. Then, the mixture was filtered through a No. 5C filter paper. The remaining solid was dried at room temperature for 24 hours and further dried at 80° C. for 1 hour to give fungicidal solid particles (P-AGSI-1). The fungicidal solid particles were pressed at a pressure of 200 kg with a tablet-forming machine to prepare a test disk having a diameter of 10 mm and a thickness of 1 mm. The test disk was subjected to the halo tests A and B to show that the widths of inhibition bands were both 2 mm.

EXAMPLE 19

1 Gram of calcium silicate particles (FLORITE, average particle diameter 10 μm, supplied by Tokuyama Soda Kabushiki Kaisha) were dispersed in a solution of 1 ml of the fungicide (AG-1) obtained in Example 16 in 300 ml of ethanol, and the mixture was stirred for 30 minutes. While the mixture was continuously stirred, the mixture was heated to remove the solvent. The mixture was heated at 120° C. for 2 hours to give fungicidal solid particles (P-AG-4). The fungicidal solid particles were subjected to the halo test to show that the width of an inhibition band was 2 mm.

EXAMPLES 20–25

Metal complex immobilized particles were prepared from various combinations of particles and fungicides shown in Table 1 in the same manner as in Example 19, and subjected to the halo test. Table 1 shows also the results. As for particles used in these Examples, TOKUSIL is a trade name for silica supplied by Tokuyama Soda Kabushiki Kaisha, talc was supplied by Wako Purechemical Industries Ltd., activate carbon and mica were supplied by Wako Purechemical Industries, Ltd., alumina was supplied by Sumitomo Chemical Co., Ltd., and α-quartz was supplied by Tatsumori Ltd.

TABLE 1

| Ex. | Particles | Diameter (μm) | Fungicide | Concentration (%)*1 | Halo test A (mm) | B (mm) |
|---|---|---|---|---|---|---|
| 20 | TOKUSIL | 0.04 | AG-1 | 2 | 3 | 3 |
| 21 | TALK | 2 | AG-1 | 2 | 2 | 2 |
| 22 | Charcoal | 10 | AG-1 | 2 | 2 | 2 |
| 23 | Mica | 10 | AG-1 | 2 | 2 | 2 |
| 24 | Alumina | 1 | AG-3 | 5 | 2 | 2 |
| 25 | α-quartz | 1.2 | AG-3 | 5 | 2 | 2 |

*1: Concentration (wt. %) of metal complex in treating solution

EXAMPLE 18

A solution of 0.34 g of TMSPEDA and 0.13 g of silver nitrate in 5 ml of methanol was stirred at room temperature for 15 minutes, and insolubles were removed by filtration to prepare a complex solution (A). Separately, a solution of 15 g of tetraethyl silicate (to be referred to as TES hereinafter) in a mixture of 15 ml of methanol with 1.5 g of a in nitric acid aqueous solution was stirred for 15 minutes, and this solution was added to the complex solution (A). The mixture was further stirred for 40 minutes to give a Fungicide

EXAMPLE 26

0.02 Gram of the fungicidal solid particles (P-AG-1) obtained in Example 16 were dispersed in a solution of 1.25 g of polystyrene having an average molecular weight of 300,000 in 25 ml of toluene under supersonic wave, and a film having a thickness of about 60 μm was formed from the above solution by a casting method. The film was transparent. When the same bacteria-inoculated agar culture solution as that used in the halo test was applied to the film and cultured at 37° C. for 24 hours, the film still remained transparent as before the application.

Comparative Example 3

A transparent film was formed in the same manner as in Example 26 except that no fungicidal solid particles were used. When bacteria was cultured on the film in the same manner as in Example 26, the bacteria grew to make the film semi-transparent.

EXAMPLE 27

60 Grams of spherical silica (1 μm, supplied by Tokuyama Soda Kabushiki Kaisha) was mixed with 40 g of the fungicidal solid particles obtained in Example 20 to prepare a filler. Then, a paste having the following composition was prepared.

Filler: 70 parts by weight
Bis-GMA: 18 parts by weight
TEGDMA: 12 parts by weight
QC: 0.15 part by weight
DMBE: 0.15 part by weight The above abbreviations stand for the following chemical names.

Bis-GMA: 2,2-bis[4-(3-methacryloxy-2-hydroxy-9-phenyl]propane
TEGDMA: triethylene glycol dimethacrylate
QC: camphorquinone
DMBE: p-dimethylbenzoic acid ethyl ester When a test disk obtained by curing the paste under the irradiation with light was tested for fungicidal activity in the same manner as in Example 26, no growth of bacteria was observed on the test disk surface.

EXAMPLE 28

1 Gram of [Ag(TMSPEDA)$_2$]NO$_3$ obtained in Example 5 was dissolved in a mixed solvent containing 47.5 ml of ethanol and 2.5 ml of water to prepare a fungicide. This fungicide was placed in a polypropylene container, and a glass fiber paper-like filter (QR200, supplied by Toyo Roshi K.K.) was immersed therein for 30 minutes. Then, the filter was dehydrated at 7 G for 8 minutes with a centrifugal dehydrator, and dried at 110° C. for 30 minutes to give a fungicidal glass fiber paper-like filter. The fungicidal glass fiber paper-like filter was subjected to the halo tests A and B to show that the widths of inhibition bands were both 1 mm.

Comparative Example 4

When the same glass fiber paper-like filter as that used in Example 28 was not subjected to fungicidal treatment, it showed that the widths of inhibition bands by the halo tests A and B were both 0 mm.

EXAMPLE 29

1 Gram of [Ag(TMSPEDA)$_2$]NO$_3$ obtained in Example 5 was dissolved in 100 ml of water to prepare a fungicide. Then, 300 ml of this fungicide was placed in a polypropylene container, and absorbent cotton (Japanese Pharmacopoeia absorbent cotton, supplied by PiP Fujimoto K.K.) was immersed therein for 30 minutes, dehydrated at 7 G with a centrifugal dehydrator for 8 minutes and dried at 110° C. for 30 minutes to give a fungicidal absorbent cotton. The fungicidal absorbent cotton was subjected to tile halo tests A and B to show that the widths of inhibition bands were both 2 mm.

EXAMPLE 30

1 Gram of [Ag(TMSPEDA)$_2$]NO$_3$ obtained in Example 5 was dissolved in 100 ml of ethanol to prepare a fungicide. Then, 300 ml of this fungicide was placed in a polypropylene container, and filter paper (Quantitative Ashless, supplied by Toyo Roshi K.K.) was immersed therein for 30 minutes, dehydrated at 7 G with a centrifugal dehydrator for 8 minutes and dried at 110° C. for 30 minutes to give fungicidal filter paper. The fungicidal filter paper was subjected to the halo tests A and B to show that the widths of inhibition bands were both 2 mm.

EXAMPLE 31

A glass sheet was washed with synthetic detergent, with ethanol and then with acetone and dried at 110° C. for 10 minutes. Then, the glass sheet was immersed in the same fungicide (AGSI-1) as that obtained in Example 18 for 20 minutes. The glass sheet was washed with ethanol and dried at 120° C. for 30 minutes to give a fungicidal glass sheet. The fungicidal glass sheet was subjected to the halo tests A and B to show that the widths of inhibition bands were both 1 mm.

EXAMPLE 32

2 Grams of [Cu(TMSPDETA)$_2$]Cl$_2$ obtained in Example 1 was dissolved in 98 ml of ethanol to prepare a fungicide (CU-1). This fungicide (CU-1) was placed in a polypropylene container, and glass fiber paper-like filter (QR200, supplied by Toyo Roshi K.K.) was immersed in the fungicide for 30 minutes. Then, the filter was dehydrated at 7 G with a centrifugal dehydrator for 8 minutes, and dried at 110° C. for 30 minutes to give a fungicidal glass fiber paper-like filter. The fungicidal glass fiber paper-like filter was subjected to the halo tests A and B to show that the widths of inhibition bands were both 0.2 mm.

EXAMPLE 33

Under nitrogen atmosphere, 35.68 g of silver nitrate AgNO$_3$ (reagent of special grade, supplied by Wako Purechemical Co., Ltd.) was added to 95.48 g of 2-(trimethoxysilyl)ethyl-2-pyridine (TMSEPYD) and the mixture was stirred for 8 hours to give a uniform yellowish solution. Thin layer chromatography showed that this yellowish solution was formed of a single component, and the results of ICP analysis (inductively coupled plasma emission spectrometry analyzer, SPS1200A, supplied by Seiko Denshi Kogyo K.K.) and CHN elemental analysis agreed with the elemental analysis values expected from [Ag(TMSEPYD)$_2$]NO$_3$. That is, the elemental analysis values were as follows. Ag: 17.2% (calculated 17.27%), Si: 9.0% (calculated 8.99%), C: 38.34% (calculated 38.46%), H: 5.55% (calculated 5.49%), N: 6.76% (calculated 6.73%).

Further, as shown in Table 2, each chemical shift in $^{13}$C-NMR of the above compound differs from those of TMSEPYD. In Table 2, chemical shifts showing peak positions were determined by using, as a reference, 206.5 ppm which was the chemical shift (long range multiplet) of (CD$_3$)$_2$CO used as a solvent for the measurement sample.

The above analysis results showed that the above-obtained compound was a metal complex in which nitrogen in pyridine ring coordinated to silver ion and which had the chemical structure of [Ag(TMSEPYD)$_2$]NO$_3$.

EXAMPLE 34

17.0 Grams of silver nitrate (supplied by Wako Purechemical Co., Ltd.) was mixed with 54.9 g of (N-[3-(triethoxysilyl)propyl]-4,5-dihydroimidazole (TESPIMD, supplied by Chisso Corp.) to give a benzene-soluble yellowish viscous liquid. ICP analysis (inductively coupled plasma emission spectrometry analyzer, SPS1200A, supplied by Seiko Denshi Kogyo K.K.) showed that the above compound contained 15.0% by weight of Ag and 7.8% by weight of Si, and electrophoresis ion analysis (capillary isotachphoresis analyzer IP-3A, supplied by Shimadzu Corporation) showed that the above compound contained 8.6% by weight of $NO_3$. Further, each chemical shift in $^{13}$C-NMR of the above compound, as shown in Table 2, differs from those of TESPIMD. Chemical shifts showing peak position were determined by using, as a reference, 206.5 ppm which was the chemical shift (long range multiplet) of $(CD_3)_2CO$ used as a solvent for the measurement sample.

Further, of the two nitrogen atoms in the imidazole ring, the nitrogen bonding to three carbon atoms has much lower capability of coordinating to metal ion than the nitrogen bonding to two carbon atom. Therefore, the nitrogen coordinating to silver ion is the nitrogen which bonds to two carbon atoms.

The above results showed that the above-obtained compound was a metal complex in which nitrogen bonding to two carbon atoms coordinated to the silver ion and which had the chemical structure of $[Ag(TESPIMD)_2]NO_3$.

TABLE 2

| Carbon[*1] | A[*2] (ppm) | A[*3] (ppm) | A-B[*4] (ppm) |
|---|---|---|---|
| | Example 33 | | |
| a | 150.582 | 152.137 | −1.555 |
| b | 122.379 | 123.354 | −0.975 |
| c | 137.562 | 139.971 | −2.409 |
| d | 123.415 | 124.696 | −1.281 |
| e | 164.881 | 164.698 | 0.183 |
| f | 32.677 | 34.964 | −2.287 |
| g | 10.816 | 11.121 | −0.305 |
| h | 51.429 | 51.032 | 0.397 |
| | Example 34 | | |
| a | 159.058 | 162.595 | −3.537 |
| b | 50.026 | 48.014 | 2.012 |
| c | 51.764 | 50.331 | 1.433 |
| d | 24.018 | 22.890 | 1.128 |
| e | 19.780 | 19.231 | 0.549 |
| f | 9.170 | 8.408 | 0.762 |
| g | 59.752 | 59.234 | 0.518 |
| h | 56.673 | 55.941 | 0.732 |

[*1]: Carbons indicated by alphabet designation in the following compounds.
[*2]: $^{13}$C-NMR chemical shift of ligands, TMSEPYD and TMSPIMD.
[*3]: $^{13}$C-NMR chemical shift of metal complex.
[*4]: Difference in $^{13}$C-NMR chemical shift between ligand and metal complex.

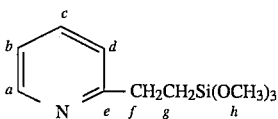

TMSEPYD (Example 33)

TABLE 2-continued

| Carbon[*1] | A[*2] (ppm) | A[*3] (ppm) | A-B[*4] (ppm) |
|---|---|---|---|

$$\underset{\substack{b \\ \phantom{x}}}{\overset{a}{N}} \diagdown \underset{c}{\diagup} NCH_2CH_2CH_2Si(OCH_2CH_3)_3 \quad \substack{d \ e \ f \quad g \quad h}$$

TMSPIMD (Example 34)

EXAMPLE 35

A solution of 0.5 g of TMSEPYD (supplied by Chisso Corp.) in 5 ml of methanol was added to a solution of 0.228 g of silver perchlorate (supplied by Wako Purechemical Co., Ltd.) in 20 ml of methanol with stirring. The solvent was removed with an evaporator to give a viscous, benzene-soluble yellowish compound.

ICP analysis (inductively coupled plasma emission spectrometry analyzer, SPS1200A, supplied by Seiko Denshi Kogyo K.K.) showed that the above compound contained 16.3% by weight of Ag and 8.5% by weight of Si, and electrophoresis ion analysis (capillary isotachphoresis analyzer IP-3A, supplied by Shimadzu Corporation) showed that the above compound contained 15.0% by weight of $ClO_4$.

Further, each chemical shift in $^{13}$C-NMR of the above compound, as shown in Table 3, differs from those of TMSEPYD. Chemical shifts showing peak positions were determined by using, as a reference, 206.5 ppm which was the chemical shift (long range multiplet) of $(CD_3)_2CO$ used as a solvent for the measurement sample, The above results showed that the above-obtained compound was a metal complex in which the nitrogen in pyridine ring coordinated to the silver ion and which had the chemical structure of $[Ag(TMSEPYD)_2]ClO_4$.

TABLE 3

| Carbon[*1] | A[*2] (ppm) | A[*3] (ppm) | A-B[*4] (ppm) |
|---|---|---|---|
| | Example 35 | | |
| a | 150.582 | 152.320 | −1.738 |
| b | 122.379 | 123.598 | −1.219 |
| c | 137.562 | 140.703 | −3.141 |
| d | 123.415 | 125.123 | −1.708 |
| e | 164.881 | 164.576 | 0.305 |
| f | 32.677 | 35.452 | −2.775 |
| g | 10.816 | 11.091 | −0.275 |
| h | 51.429 | 50.788 | 0.638 |

[*1]: Carbons indicated by alphabet designation in the following compound (TMSEPYD).
[*2]: $^{13}$C-NMR chemical shift of ligand, TMSEPYD.
[*3]: $^{13}$C-NMR chemical shift of metal complex.
[*4]: Difference in $^{13}$C-NMR chemical shift between ligand and metal complex.

$$\underset{a}{\diagup}\underset{N}{\diagdown}\underset{e\ f\ g\ h}{-CH_2CH_2Si(OCH_3)_3}$$

(pyridine ring with positions b, c, d)

EXAMPLE 36

1 Gram of the metal complex obtained in Example 33 was dissolved in a mixed solvent containing 49 ml of methanol and 1 ml of water to prepare a metal complex solution.

1 Gram of silica particles having a particle diameter of 1.7 μm were dispersed in 25 ml of the above metal complex solution, and the mixture was stirred at room temperature for 20 minutes and filtered through No. 5C filter paper. The remaining solid was washed with methanol, dried at room temperature for 24 hours and further dried at 80° C. for 1 hour to give metal complex immobilized particles. The above-prepared particles were pressed at a pressure of 200 kg with a tablet-forming machine to prepare a test disk having a diameter of 10 mm and a thickness of 1 mm. The test disk was subjected to the halo tests A and B to show that the widths of inhibition bands were both 3.5 mm or that the metal complex immobilized particles exhibited sufficient fungicidal activity.

Further, metal complex immobilized particles were prepared from the metal complex obtained in Example 34 in the same manner as above, and a test disk for the evaluation of fungicidal activity was also prepared in the same manner as above. The test disk was subjected to the halo tests A and B to show that the widths of inhibition bands were both 3.5 mm or that the metal complex immobilized particles exhibited sufficient fungicidal activity.

Further, metal complex immobilized particles were prepared from the metal complex obtained in Example 35 in the same manner as above, and a test disk for the evaluation of fungicidal activity was also prepared in the same manner as above. The test disk was subjected to the halo tests A and B to show that the widths of inhibition bands were both 3.5 mm or that the metal complex immobilized particles exhibited sufficient fungicidal activity.

EXAMPLE 37

1.8 Grams of $[Ag(TMSEPYD)_2]NO_3$ obtained in Example 33 was dissolved in 50 ml of methanol to prepare a metal complex solution. Then, a metal complex immobilized particles were prepared as follows. 300 Grams of spherical silica particles having an average particle diameter of 0.85 μm (ADOMA FINE, supplied by Tatsumori Ltd.) were dispersed in 300 ml of methanol to form a slurry. While the slurry was stirred, 50 ml of the above metal complex solution was added dropwise to the slurry. Then, methanol in the mixture was removed with a rotary evaporator at 40° C. The remainder was dried at 120° C. with a vacuum dryer for 30 minutes to give metal complex immobilized particles (AG-SO).

An ethylene-propylene copolymer having a melt flow index, at 230° C., of 8.0 g/10 minutes in an amount of 99.5% by weight and 0.5% by weight of the metal complex immobilized particles (AG-SO) were mixed with a Henschel mixer. The mixture was extruded and pelletized with a single-screw extruder at a resin temperature of 210° C. to give fungicidal resin pellets (a).

On the other hand, polypropylene having a melt flow index, at 230° C., of 2.0/10 minutes was extruded in a sheet form with a T-die extruder at a resin temperature of 240° C., and the extrudate was cooled and solidified with a chill roll maintained at 40° C. to give a sheet having a thickness of 1.2 mm. The sheet was monoaxially stretched with a heating roll at 150° C. at a stretch ratio of 4.8 to give a monoaxially stretched sheet having a thickness of 240 μm.

Then, the above-obtained fungicidal resin pellets (a) were extruded in a sheet form with a T-die extruder at a resin temperature of 210° C., and the resultant sheet and the above monoaxially stretched sheet were laminated on each other on a roll maintained at 70° C. to give a two-layered sheet having a thickness of 250 μm.

Thereafter, the above two-layered sheet was widthwise stretched at a stretch ratio of 10 with a lateral stretcher at 160° C. to give a colorless transparent fungicidal resin film whose propylene layer had a thickness of 24.0 μm and whose fungicidal resin composition layer was 1 μm. When the so-obtained fungicidal resin film was examined by a fungicidal activity test using a culturing method to be described later, the numbers of surviving *Escherichia coli* and *Bacillus subtilis* were both zero, or it was found that the fungicidal resin film had fungicidal activity.

5 Grams of tofu (soybean curd) was placed in a bag (80×120 mm) formed of the above fungicidal resin film and stored at 25° C. After one week, any alteration in the tofu was not observed.

Antibacterial activity test using culturing method

The fungicidal resin film was evaluated for its fungicidal activity as follows. A film was formed into a bag (80×120 mm). When the film had a multi-layered structure and when one surface alone had fungicidal activity, the inner wall of the bag had fungicidal activity. A bacteria suspension in an amount of 0.1 ml was dropped inside the bag, and air was exhausted from inside the bag. Then, the bag was stored at 37° C. for 24 hours, and surviving bacteria within the bag was washed out with a phosphoric acid buffer solution (5 ml). The number of surviving bacteria in the wash liquid was counted by using an agar medium plate. For the preparation of the bacteria solution, *Escherichia coli* and *Bacillus subtilis* were used respectively.

EXAMPLE 38

Polypropylene having a melt flow index, at 230° C., of 2.0/10 minutes was extruded in a sheet form at a resin temperature of 240° C., and the extrudate was cooled and solidified with a chill roll maintained at 40° C. to give a sheet having a thickness of 1.1 mm. Further, the sheet was monoaxially stretched with a heat roll stretcher at 150° C. at a stretch ratio of 4.8 to give a monoaxially stretched sheet having a thickness of 230 μm.

Then, the same fungicidal resin pellets (a) as those obtained in Example 37 were extruded in a sheet form with a T-die extruder at a resin temperature of 210° C., and the resultant sheet and the above monoaxially stretched sheet were laminated on each other on a roll maintained at 70° C. to give a two-layered sheet having a thickness of 240 μm.

Further, the same fungicidal resin pellets (a) as those obtained in Example 37 were extruded in a sheet form with a T-die extruder, and the resultant sheet was laminated on the monoaxially stretched sheet side of the above two-layered sheet to give a three-layered sheet having a thickness of 250 μm.

The so-obtained three-layered sheet was stretched with a lateral stretcher at 160° C. at a stretch ratio of 10 to give a colorless transparent fungicidal resin film whose polypropylene base layer had a thickness of 23.0 μm, whose fungicidal resin composition layers had a thickness of 1.0 μm each and whose total thickness was 25.0 μm.

The above fungicidal resin film was subjected to the fungicidal activity test using a culturing method to show that the number of surviving bacteria was zero. 5 Grams of tofu (soybean curd) was placed in a bag (80×120 mm) formed of the above fungicidal resin film and stored at 25° C. for 1 week. When visually observed, the tofu showed no alteration and was stored in a good condition.

EXAMPLE 39

1.8 Grams of [Cu(TMSPEDA)$_2$]Cl$_2$ obtained in Example 2 was dissolved in 50 ml of methanol to prepare a metal complex solution. Then, metal complex immobilized particles were prepared as follows. 300 Grams of spherical silica particles having an average particle diameter of 0.85 µm (ADOMA FINE, supplied by Tatsumori Ltd) were dispersed in 300 ml of methanol to form a slurry. While the slurry was stirred, the above metal complex solution was added dropwise to the slurry. Then, methanol in the mixture was removed with a rotary evaporator at 40° C. The remainder was dried at 120° C. with a vacuum dryer for 30 minutes to give metal complex immobilized particles (CU-SO).

An ethylene-propylene copolymer having a melt flow index, at 230° C., of 8.0 g/10 minutes in an amount of 98.0% by weight and 2.0% by weight of the metal complex immobilized particles (CU-SO) were mixed with a Henschel mixer. The mixture was extruded and pelletized with a single-screw extruder at a resin temperature of 210° C. to give fungicidal resin pellets.

Polypropylene having a melt flow index, at 230° C., of 2.0/10 minutes was extruded in a sheet form with a T-die extruder at a resin temperature of 240° C., and the extrudate was cooled and solidified with a chill roll maintained at 40° C. to give a sheet having a thickness of 1.2 mm. The sheet was monoaxially stretched with a heating roll at 150° C. at a stretch ratio of 4.8 to give a monoaxially stretched sheet having a thickness of 240 µm.

Then, the above-obtained fungicidal resin pellets were extruded in a sheet form with a T-die extruder at a resin temperature of 210° C., and the resultant sheet and the above monoaxially stretched sheet were laminated on each other on a roll maintained at 70° C. to give a two-layered sheet having a thickness of 250 µm.

Thereafter, the above two-layered sheet was stretched at a stretch ratio of 10 with a lateral stretcher at 160° C. to give a colorless transparent fungicidal resin film whose propylene layer had a thickness of 24.0 µm and whose fungicidal resin composition layer was 1 µm. When the so-obtained fungicidal resin film was examined by the fungicidal activity test using a culturing method, the numbers of surviving *Escherichia coli* and *Bacillus subtilis* were both zero, or it was found that the fungicidal resin film had fungicidal activity.

5 Grams of tofu (soybean curd) was placed in a bag (80×120 mm) formed of the above fungicidal resin film, and stored at 25° C. for 1 week. When visually observed, the tofu showed no alteration and was stored in a good condition.

EXAMPLE 40

1.6 Grams of [Ag(TESPIMD)$_2$]NO$_3$ obtained in Example 34 was dissolved in 50 ml of methanol to prepare a metal complex solution.

Then, metal complex immobilized particles (AGIM-SO) were prepared in the same manner as in Example 39 except that the metal complex solution used in Example 39 was replaced with the above metal complex solution. And, fungicidal pellets were also prepared using the above pellets in the same manner as in Example 39.

Further, a colorless transparent fungicidal resin film having a thickness of 25.0 µm was obtained in the same manner as in Example 39 except that the fungicidal pellets used in Example 39 were replaced with the above fungicidal pellets.

When the so-obtained fungicidal resin film was examined by the fungicidal activity test using a culturing method, the numbers of surviving *Escherichia coli* and *Bacillus subtilis* were both zero, or it was found that the fungicidal resin film had fungicidal activity.

5 Grams of tofu (soybean curd) was placed in a bag (80×120 mm) formed of the above fungicidal resin film, and stored at 25° C. for 1 week, When visually observed, the tofu showed no alteration and was stored in a good condition.

Comparative Example 5

An ethylene-propylene copolymer having a melt flow index, at 230° C., of 8.0 g/10 minutes in an amount of 99.5% by weight and 0.5% by weight of silver ion-exchanged zeolite (average particle diameter 1.6 µm) were mixed with a Henschel mixer. Then, the mixture was extruded and pelletized with a single-screw extruder at a resin temperature of 210° C. to give fungicidal resin pellets.

The fungicidal resin pellets color-changed to yellow. The fungicidal activity thereof was examined by forming it into a film in the following Comparative Example 6.

Comparative Example 6

A biaxially stretched fungicidal resin film was prepared in the same manner as in Example 37 except that the fungicidal resin pellets obtained in Example 37 were replaced with the fungicidal resin pellets obtained in Comparative Example 5. When the so-obtained fungicidal resin film was examined by the fungicidal activity test using a culturing method, the numbers of surviving *Escherichia coli* and *Bacillus subtilis* were both zero. However, when 5 g of tofu (soybean curd) was placed in a bag (80×120 mm) formed of the above fungicidal resin film, and stored at 25° C. for 1 week, the tofu had a portion of which the color turned black and a portion where yellow mold occurred.

Comparative Example 7

A colorless transparent fungicidal resin film was prepared in the same manner as in Example 37 except that the metal complex immobilized particles (AG-SO) were replaced with spherical silica (average particle diameter 1.5 µm, SILTONE AMT, supplied by Mizusawa Chemical Co., Ltd) on which no metal complex was immobilized.

The fungicidal activity of the so-obtained fungicidal resin film was examined by using a culturing method. The numbers of surviving *Escherichia coli* and *Bacillus subtilis* were $3.2 \times 10^3$ and $1.8 \times 10^3$ respectively, or it was found that the above fungicidal resin film had no fungicidal activity. When 5 g of tofu (soybean curd) was placed in a bag (80×120 mm) formed of the above fungicidal resin film, and stored at 25° C. for 1 week, yellow mold occurred on the tofu surface.

EXAMPLE 41

A solution of [Ag(TMSEPYD)$_2$]NO$_3$, [Ag(TMSPEDA)$_2$]NO$_3$ or silver nitrate in methanol was added to 5 g of silica particles having a particle diameter of 1.7 µm such that the silver content based on the silica particles was 1.2% by weight. The so-prepared mixtures were separately kneaded in a mortar until the solvent was volatilized.

The resultant powders were dried with a dryer at 120° C. for 2 hours to give three kinds of fungicidal particles. For examining the durability of the fungicidal activity of each kind of fungicidal particles, the elution behavior of silver ion was examined.

A suspension of 1 g of the fungicidal particles in 22 ml of ion-exchanged water was stirred with a rotary shaker for 20 minutes, and centrifugally separated into particles and a liquid in which silver concentration was measured by ICP. The above procedure was taken as one washing cycle. This procedure was repeated, and the dependence of the concentration of silver eluted from the fungicidal particles on number of washes was shown in Table 9.

In FIG. 9, the concentration of eluted silver ion from the particles surface-treated with $[Ag(TMSEPYD)_2]NO_3$ or $[Ag(TMSPEDA)_2]NO_3$ is indicated by 1-○-○- or 2-●-●-, and the concentration of eluted silver ion from the particles surface treated with silver nitrate is indicated by 3-■-■-.

The fungicidal particles obtained by immobilizing $[Ag(TMSEPYD)_2]NO_3$ on surfaces of silica particles and the fungicidal particles obtained by immobilizing $[Ag(TMSPEDA)_2]NO_3$ on surfaces of silica particles showed that the concentration of eluted silver ion did not greatly decrease with washing after a few washing cycles and that the concentration of eluted silver ion was still at least 1 ppm even after the 14th washing cycle. In contrast, the particles treated with silver nitrate showed that the concentration of eluted silver ion rapidly decreased as the washing cycle increased, and that the concentration of eluted silver decreased to only about 0.1 ppm after tile 14th washing cycle.

When the fungicidal particles after the 14th washing cycle were subjected to the halo tests A and B, the fungicidal particles obtained by immobilizing $[Ag(TMSEPYD)_2]NO_3$ on surfaces of silica particles and the fungicidal particles obtained by immobilizing $[Ag(TMSPEDA)_2]NO_3$ on surfaces of silica particles showed that the widths of inhibition bands were both 1.2 mm, while the particles treated with silver nitrate showed that the widths of inhibition bands were both less than 0.1 mm, or its fungicidal activity was very low.

The above results show that the particles treated with the metal complex of tile present invention are fungicidal particles having durability, clearly differing from the particles treated with silver nitrate.

EXAMPLE 42

A silver complex $[Ag(TMSEPYD)_2]NO_3$ was dissolved in ethanol to prepare a solution having a silver concentration of 860 ppm.

A polyethylene terephthalate (PET) sheet (30×30×0.1 mm) was immersed in the above solution for 30 minutes, then air-dried at room temperature for 30 minutes and then dried at 50° C. for 30 minutes. Further, the sheet was washed with ethanol to remove $[Ag(TMSEPYD)_2]NO_3$ which was not immobilized on the sheet surface, and the sheet was dried at room temperature for 30 minutes and at 50° C. for 30 minutes to give a fungicidal PET sheet.

When the above fungicidal PET sheet was subjected to the halo tests A and B, the widths of inhibition bands were both 0.5 mm, or the fungicidal PET sheet showed fungicidal activity.

EXAMPLE 43

$[Ag(TMSEPYD)_2]NO_3$ obtained in Example 33 was dissolved in ethanol (reagent of special grade, supplied by Wako Purechemical Co., Ltd.) to prepare a metal complex solution having a metal complex concentration of 0.01% by weight (concentration as silver 17 ppm, molar concentration $1.6 \times 10^{-7}$ mol/g).

6.35 Grams of the above metal complex solution and 6.7 g of liquefied petroleum gas (LPG) as a propellant were charged into an aluminum container, and the container was sealed to give a fungicidal spray solution usable with a sprayer.

The above fungicidal spray solution was sprayed to filter paper for about 0.5 second at a distance of 5 cm between the sprayer and the paper, and the filter paper was subjected to the halo tests A and B to show that the widths of inhibition bands were both 0.5 mm.

EXAMPLE 44

1 Part by weight of silica (Reolosil, supplied by Tokuyama Soda Kabushiki Kaisha) was added to, and mixed with, 100 parts by weight of the same metal complex solution as that prepared in Example 43, to give a silica-dispersed metal complex solution.

A fungicidal spray solution was prepared using the above silica-dispersed metal complex in the same manner as in Example 43.

The above fungicidal spray solution was sprayed to filter paper, and the filter paper was subjected to the halo tests A and B to show that the widths of inhibition bands were both 0.5 mm.

Comparative Example 8

A typical quarternary ammonium salt, n-Octadecyldimethyl[ 3-(trimethoxysilyl)-propyl]ammonium chloride (50% methanol solution, supplied by Chisso Corp.), which was well a known fungicide, was dissolved in ethanol (reagent of special grade, supplied by Wako Purechemical Co., Ltd.) to give a solution having a concentration of 0.008% by weight (molar concentration; $1.6 \times 10^{-}$mol/g, the same molar concentration as that in Example 34).

The above quaternary ammonium salt solution and liquefied petroleum gas were charged into an aluminum container in the same manner as in Example 49 to obtain a spray solution. The spray solution was sprayed to filter paper, and the filter paper was subjected to the halo tests A and B to show that the widths of inhibition bands were both 0 mm, or the filter paper showed no fungicidal activity.

EXAMPLE 45

The minimum growth inhibition concentration (MIC) of $[Ag(TMSEPYD)_2]NO_3$ obtained in Example 33 was determined as follows. Table 4 shows the results.

Method of measurement of minimum growth inhibition concentration (MIC)

The silver complex was diluted with dimethyl sulfoxide to prepare a sample stock solution having a concentration of 2,000 µg/ml. This sample stock solution was diluted with dimethyl sulfoxide to prepare a 1,000, 200, 100, 20 and 2 µg/ml dilution series, and 0.5 ml was aseptically taken from each dilution into a petri dish and mixed with 9.5 ml of an agar medium for the measurement of susceptibility (supplied by Nissui Seiyaku K.K.) to prepare plates having six concentrations such as 100, 50, 10, 5, 1 and 0.1 µg/ml.

When the test microorganism were bacteria (*Escherichia coli, Staphylococcus aureus, Qseudomonas aeruginosa, Bacillus subtilis*), test microorganism suspensions were prepared according to the MIC measurement method (1980) specified by Japan Society of Chemotherapy, and applied to chemical-mixed plate media in an amount of one platinum loop. The microorganism solutions were cultured at 37° C. for 24 hours, and the minimum concentration at which no growth was observed was taken as MIC.

As for test microorganism, *Bacillus subtilis*, a bacterial spore liquid was applied.

When the test microorganisms were fungi (*Aspergillus niger, Penicillium funiculosum, Aureobasidium pullulans, Cladosporium cladosporioides*), Suspensions of spores of test mold were prepared according to JIS Z 2911-1981, and each of the suspensions was applied to plate medium containing the test material (supplied by Nissui Seiyaku K.K.) in an amount of one platinum loop. The spores of test mold were cultured at 27° C. for 7 days, and the minimum concentration at which no growth was observed was taken as MIC.

TABLE 4

Minimum Inhibitory Concentration (MIC)
(Antimicrobial spectrum of silver complex)

| Microbe | $[Ag(TMSEPYD)_2]NO_3$ (μg/μl) |
|---|---|
| *Escherichia coli* IFO 3301 | 100 |
| *Pseudomonas aeruginosa* IFO 3445 | 100 |
| *Bacillus subtilis* ATCC 6633 | 100 |
| *Staphylococcus aureus* IFO 12732 | 50 |
| *Aspergillus niger* ATCC 9642 | 50 |
| *Penicillium funiculosum* ATCC 9644 | 50 |
| *Aureobasidium pullulans* LAMF 24 | 50 |
| *Cladosporium cladosporioides* IFO 6348 | 50 |

BRIEF DESCRIPTION OR DRAWINGS

Figure 1:
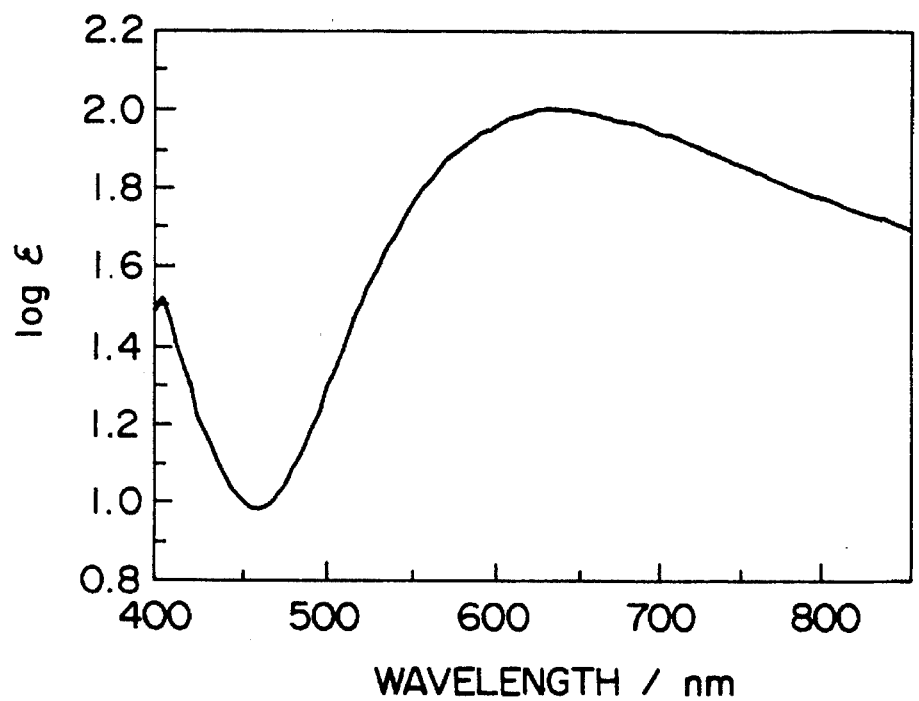
FIG. 1 shows tile visible absorption spectrum of a methanol solution of the metal complex obtained in Example 1.
Figure 3:
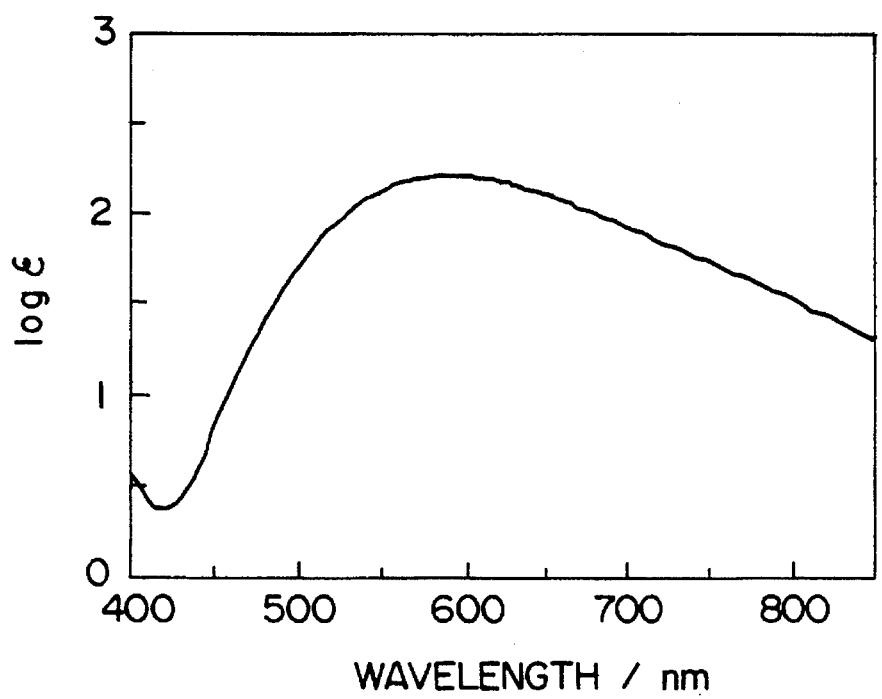
FIG. 3 shows the visible absorption spectrum of a methanol solution of the metal complex obtained in Example 2.
Figure 2:
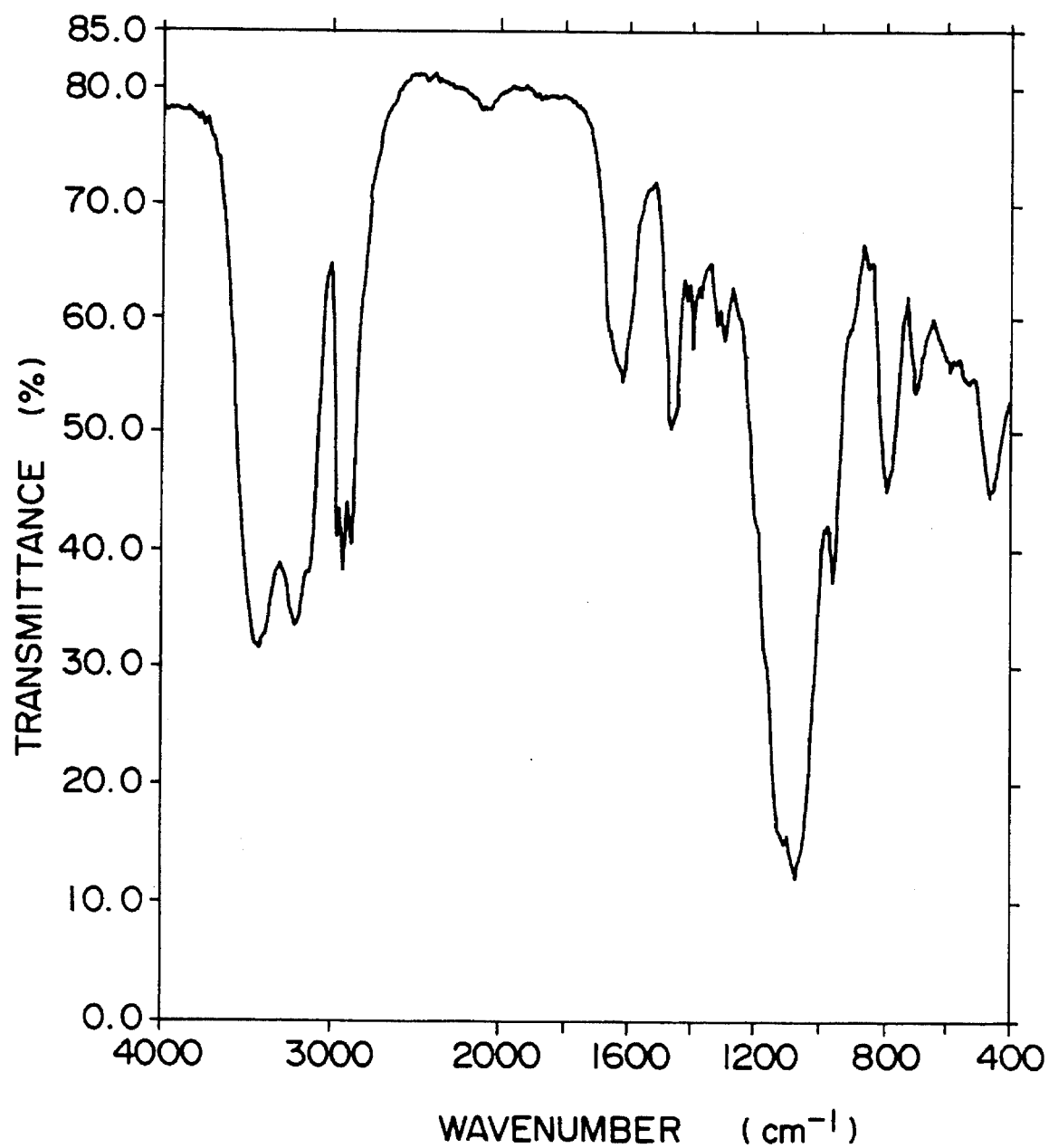
FIG. 2 shows the IR spectrum of a methanol solution of the metal complex obtained in Example 1.
Figure 4:
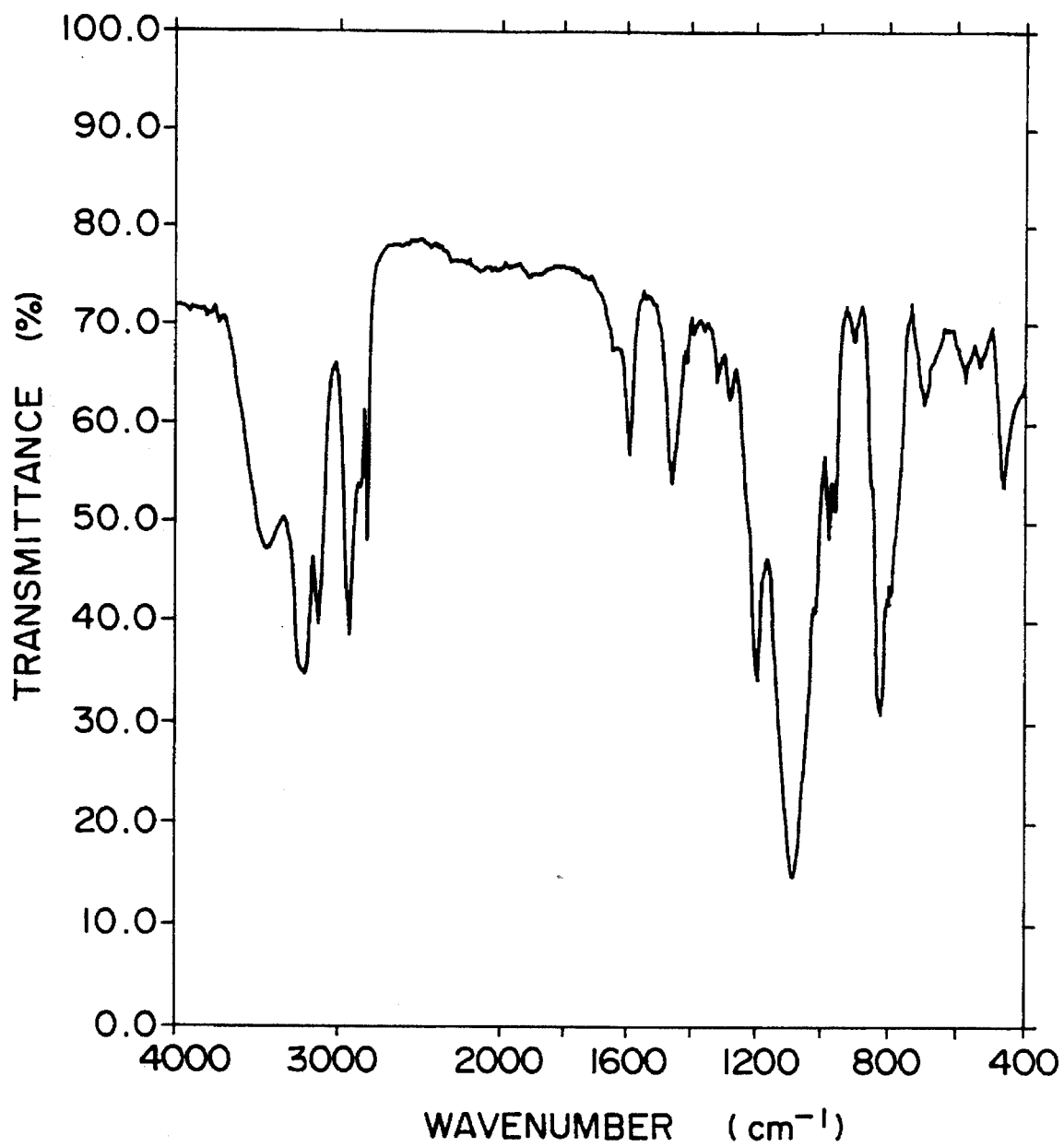
FIG. 4 shows the IR spectrum of a methanol solution of the metal complex obtained in Example 2.
Figure 5:
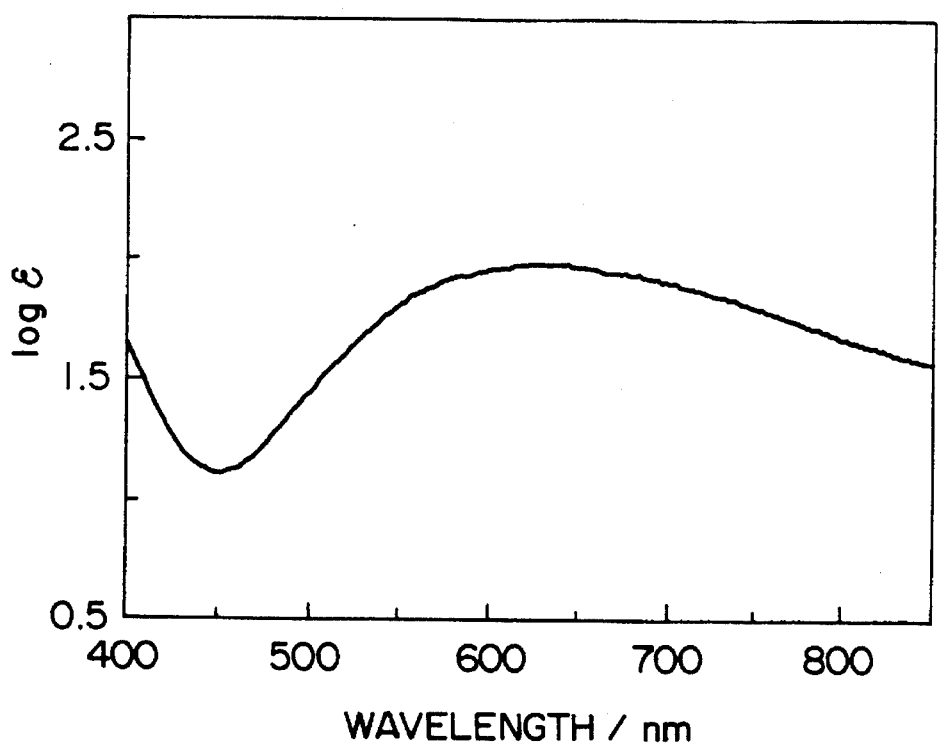
FIG. 5 shows the visible absorption spectrum of a methanol solution of the metal complex obtained in Example 3.
Figure 9:
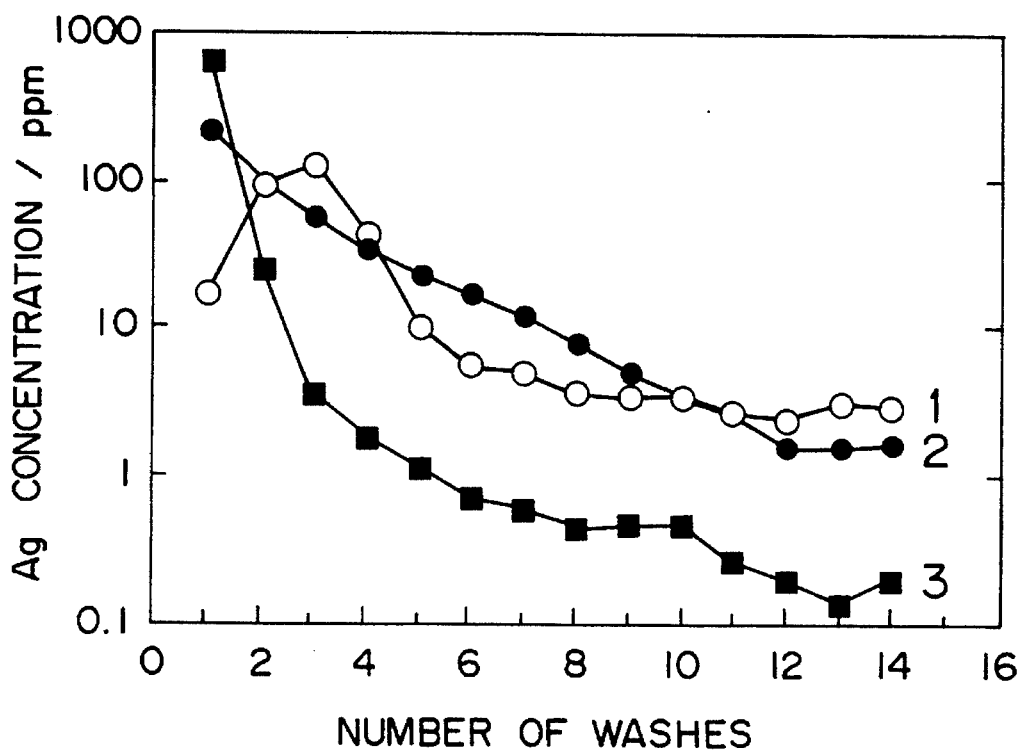
Figure 6:
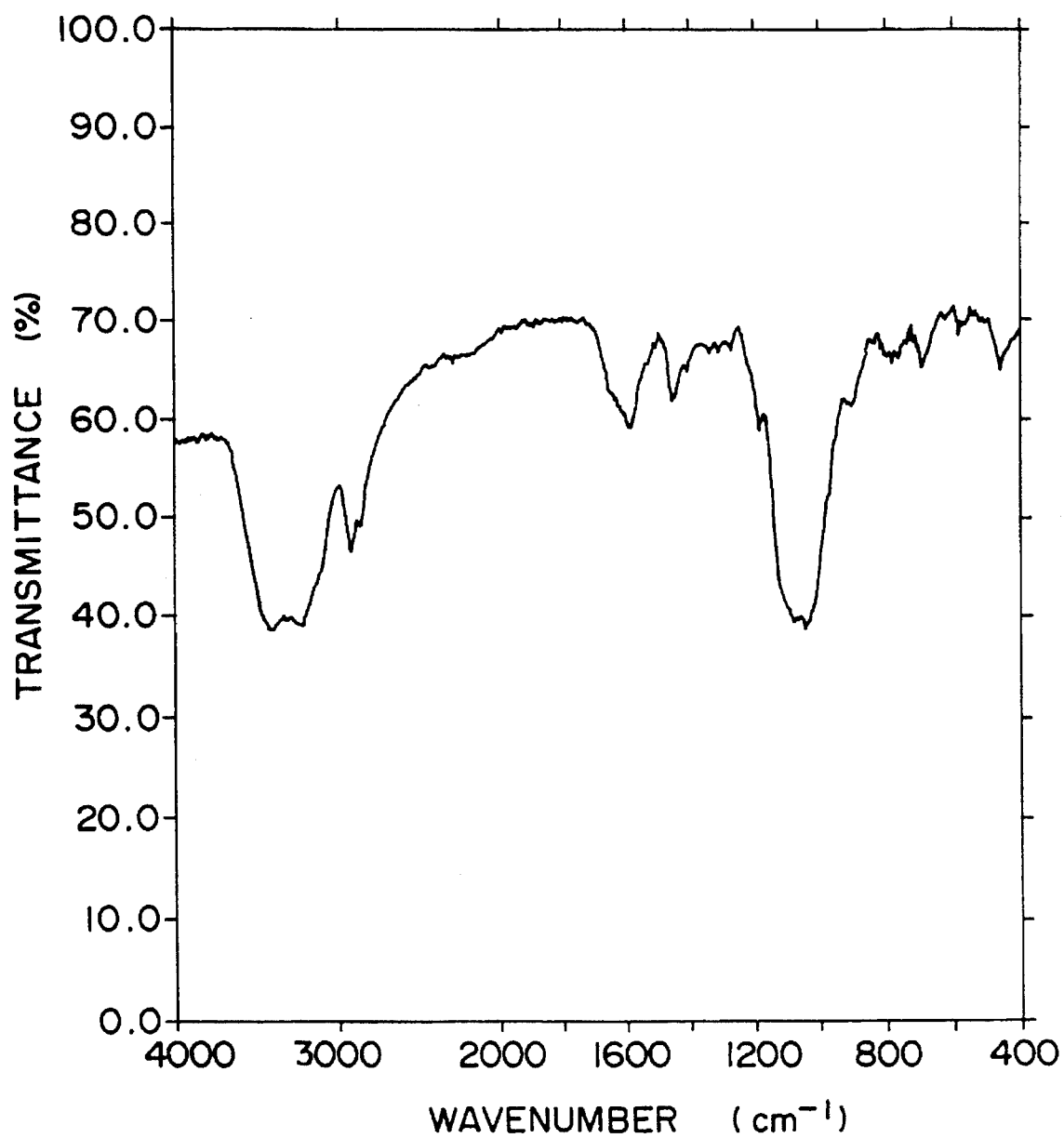
FIG. 6 shows the IR spectrum of a methanol solution of the metal complex obtained in Example 3.
Figure 7:
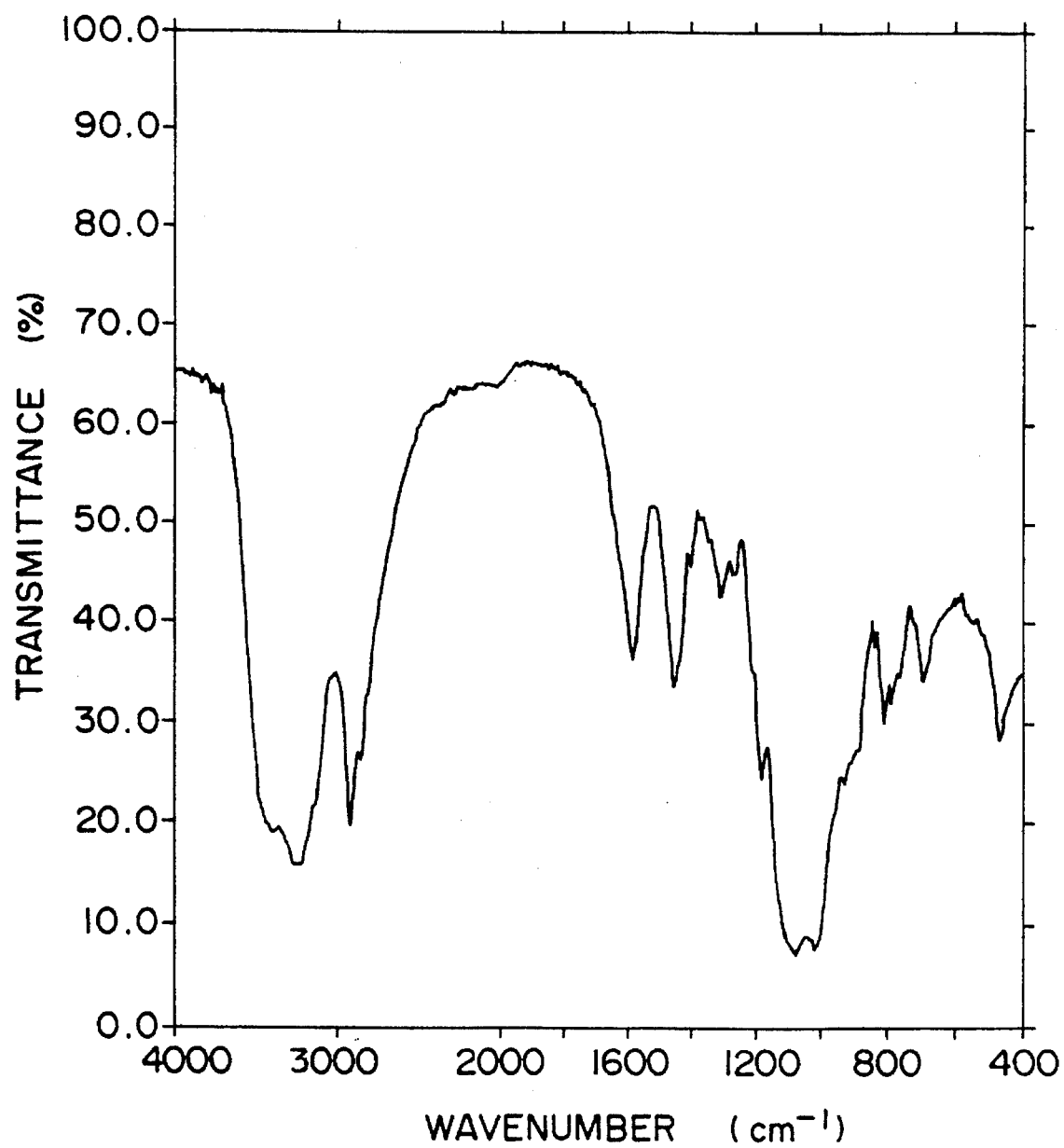
FIG. 7 shows the IR spectrum of a methanol solution of the metal complex obtained in Example 4.
Figure 8:
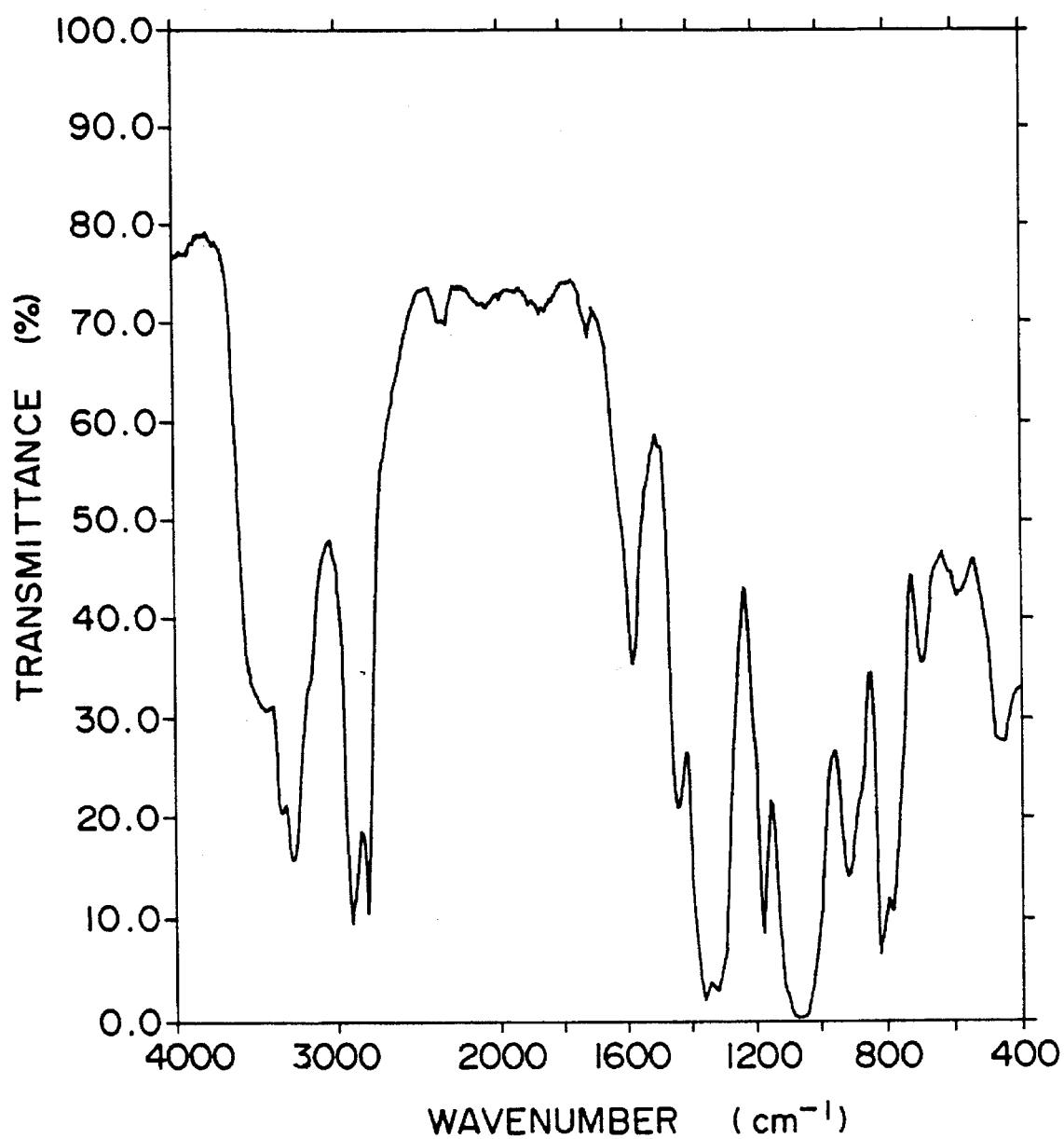
FIG. 8 shows the IR spectrum of a methanol solution of the metal complex obtained in Example 5.

FIG. 9 shows the concentrations of eluted silver ions from three kinds of fungicidal particles obtained in Example 41 relative to number of washes, in which numeral 1 indicates the concentration of eluted silver ion from the particles surface-treated with $[Ag(TMSEPYD)_2]NO_3$, numeral 2 indicates the concentration of eluted silver ion from the particles surface-treated with or $[Ag(TMSPEDA)_2]NO_3$, and numeral 3 indicates the concentration of eluted silver ion from the particles surface treated with silver nitrate.

What is claimed is:

1. A fungicidal composition containing, as an active ingredient, a metal complex of the formula (I), $$[M\{W-Si(OA^1)_k A^2_{3-k}\}_g]Z_f \quad (I)$$

wherein

M is silver ion, copper ion or zinc ion, each of $A^1$ and $A^2$ is independently a lower alkyl group f is 1 or 2, k is an integer of 1 to 3, g is an integer of 1 to 6, Z is an anion, and W is a group of the formula (a-1) or (a-2), $$\begin{array}{c} R^1 \\ \diagdown \\ R^2 \diagup \end{array} N-(CH_2)_m-(N)_t-(CH_2)_n-(N)_p-(CH_2)_q- \quad (a\text{-}1)$$

$$X-(CH_2)_r-(N)_p-(CH_2)_q- \quad (a\text{-}2)$$
       $\quad\quad\quad\quad\quad\quad |$
       $\quad\quad\quad\quad\quad R^3$ in which:

each of $R^1$, $R^2$, $R^3$ and $R^4$ is independently a hydrogen atom, a lower alkyl group or a lower aminoalkyl group, or $R^1$ and $R^2$ together form a group of $-CH_2CH_2NHCH_2CH_2-$, m is 0, 2 or 3, n is 0, 2 or 3, p is 0 or 1, q is an integer of 1 to 6, t is 0 or 1, r is 0, 1 or 2, and X is a nitrogen-containing heterocyclic group, provided that when p in the formula (a-1) is 0, n is 0, that when t in the formula (a-1) is 0, m is 0, and that when r in the formula (a-2) is 0, p is 0, or metal complex immobilized particles obtained by immobilizing the above metal complex on solid particle surfaces, and a fungicidal carrier therefor.

2. A fungicidal composition of claim 1, wherein the metal complex of the formula (I) is represented by the following formula (I-a-2), $$[Ag\{X-(CH_2)_r-(N)_p-(CH_2)_q-Si(OA^1)_k A^2_{3-k}\}_2]Z \quad (\text{I-a-2})$$
           $\quad\quad\quad\quad |$
           $\quad\quad\quad R^3$ wherein X, $R^3$, $A^1$, $A^2$, Z, r, p, q and k are as defined in the formula (I).

3. A fungicidal composition of claim 2, wherein X is a 5-membered or 6-membered heterocyclic ring containing 1 or 2 nitrogen atoms.

4. The fungicide of claim 2, wherein the formula (I-a-2) is represented by the following formula, $$[Ag\{X-(CH_2)_q-Si(OA^1)_k A^2_{3-k}\}_2]Z$$

wherein X, $A^1$, $A^2$, Z, q, and k are as defined in the formula (I).

5. A fungicidal composition of claim 2, wherein k is 3.

6. A fungicidal composition of claim 1 wherein the metal complex of the formula (I) is represented by the following formula (I-a-1), $$[M\{\begin{array}{c} R^1 \\ \diagdown \\ R^2 \diagup \end{array} N-(CH_2)_m-(N)_t-(CH_2)_n-(N)_p-(CH_2)_q-Si(OA^1)_k A^2_{3-k}\}_g]Z_f \quad (\text{I-a-1})$$

wherein M, $R^1$, $R^2$, $R^3$, $R^4$, $A^1$, $A^2$, Z, f, g, m, n, p, q, t and k are as defined in the above formula (I).

7. A fungicidal composition of claim 6, wherein all of $R^1$, $R^2$, $R^3$ and $R^4$ are hydrogen atoms.

8. A fungicidal composition of claim 6, wherein k is 3.

9. A fungicidal composition of claim 1, wherein the solid particles have an active group reactive with an alkoxysilyl group on the surface.

10. A fungicidal composition of claim 1, wherein the solid particles are inorganic solid particles of at least one member selected from the group consisting of silica, titania, zirconia, alumina, zeolite, calcium silicate, apatite, glass and clay mineral particles.

11. A fungicidal composition of claim 1, wherein the solid particles are inorganic solid particles of at least one member selected from the group consisting of silica, titania, alumina, calcium silicate and glass.

12. A fungicidal composition according to claim 1 in the form of a liquid mixture, the fungicidal carrier being a liquid medium.

13. A fungicidal composition according to claim 12 in the form of a spray solution.

14. A fungicidal spray solution according to claim 13 containing the metal complex of the formula (I) as a fungicidal component.

15. A fungicidal composition according to claim 12 in the form of a coating solution.

16. A fungicidal composition according to claim 15 wherein the fungicidal component is metal complex immobilized particles obtained by immobilizing the metal complex of formula (I) on solid particle surfaces.

17. A fungicidal composition according to claim 1 which comprises metal complex immobilized particles obtained by immobilizing the metal complex of formula (I) on solid particle surfaces, said particles being dispersed in a resin.

18. A fungicidal composition according to claim 17 in the form of a film.

19. A fungicidal composite film which is a laminated film formed by laminating a film formed of the fungicidal resin composition recited in claim 18 on at least one surface of another film.

20. Metal complex immobilized particles obtained by immobilizing a metal complex of the formula (I)

$$[M\{W-Si(OA^1)_k A_{3-k}^2\}_g]Z_f \qquad (I)$$

where in:

M is silver ion, copper ion or zinc ion, each of $A^1$ and $A^2$ is independently a lower alkyl group, f is 1 or 2, k is an integer of 1 to 3, g is an integer of 1 to 6, Z is an anion, and W is a group of the formula (a-1) or (a-2),

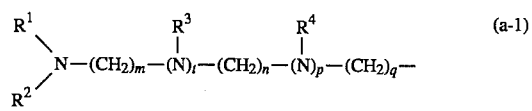
(a-1)

(a-2)

in which:

each of $R^1$, $R^2$, $R^3$ and $R^4$ is independently a hydrogen atom, a lower alkyl group or a lower aminoalkyl group, or $R^1$ and $R^2$ together form a group of —CH$_2$CH$_2$NHCH$_2$CH$_2$—, m is 0, 2 or 3, n is 0, 2 or 3, p is 0 or 1, q is an integer of 1 to 6, t is 0 or 1, r is 0, 1 or 2, and X is a nitrogen-containing heterocyclic group, provided that when p in the formula (a-1) is 0, n is 0, that when t in the formula (a-1) is 0, m is 0, and that when r in the formula (a-2) is 0, p is 0, on the surfaces of solid particles.

21. The metal complex immobilized particles of claim 20, wherein the solid particles have an active group reactive with an alkoxysilyl group.

22. The metal complex immobilized particles of claim 20, wherein the solid particles are inorganic solid particles of at least one member selected from the group consisting of silica, titania, zirconia, alumina, zeolite, calcium silicate, apatite, glass and clay mineral particles.

23. The metal complex immobilized particles of claim 20, wherein the solid particles are inorganic solid particles of at least one member selected from the group consisting of silica, titania, alumina, calcium silicate and glass.

* * * * *